US011149274B2

(12) United States Patent
Jo et al.

(10) Patent No.: US 11,149,274 B2
(45) Date of Patent: Oct. 19, 2021

(54) METHODS AND COMPOSITIONS FOR MANAGING VASCULAR CONDITIONS

(71) Applicants: Emory University, Atlanta, GA (US); Georgia Tech Research Corporation, Atlanta, GA (US)

(72) Inventors: Hanjoong Jo, Marietta, GA (US); Dongju Son, Decatur, GA (US); Wakako Takabe, Atlanta, GA (US); Sandeep Kumar, Atlanta, GA (US); Haiwei Qiu, Decatur, GA (US); Chanwoo Kim, Decatur, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 16/702,427

(22) Filed: Dec. 3, 2019

(65) Prior Publication Data

US 2020/0095583 A1 Mar. 26, 2020

Related U.S. Application Data

(60) Division of application No. 16/107,936, filed on Aug. 21, 2018, now Pat. No. 10,538,766, which is a continuation of application No. 14/772,978, filed as application No. PCT/US2014/023396 on Mar. 11, 2014, now abandoned.

(60) Provisional application No. 61/916,449, filed on Dec. 16, 2013, provisional application No. 61/904,026, filed on Nov. 14, 2013, provisional application No. 61/776,201, filed on Mar. 11, 2013.

(51) Int. Cl.
| | | |
|---|---|---|
| *C12N 15/11* | (2006.01) | |
| *C12N 15/113* | (2010.01) | |
| *A61K 47/64* | (2017.01) | |
| *A61K 47/54* | (2017.01) | |
| *A61K 47/60* | (2017.01) | |
| *A61K 9/14* | (2006.01) | |
| *A61K 31/713* | (2006.01) | |
| *A61K 45/06* | (2006.01) | |
| *A61L 31/04* | (2006.01) | |
| *A61L 31/10* | (2006.01) | |
| *A61L 31/12* | (2006.01) | |
| *A61L 31/14* | (2006.01) | |
| *A61L 31/16* | (2006.01) | |
| *A61K 47/61* | (2017.01) | |
| *A61K 47/55* | (2017.01) | |

(52) U.S. Cl.
CPC .......... *C12N 15/113* (2013.01); *A61K 9/14* (2013.01); *A61K 31/713* (2013.01); *A61K 45/06* (2013.01); *A61K 47/549* (2017.08); *A61K 47/55* (2017.08); *A61K 47/60* (2017.08); *A61K 47/61* (2017.08); *A61K 47/64* (2017.08); *A61L 31/04* (2013.01); *A61L 31/10* (2013.01); *A61L 31/125* (2013.01); *A61L 31/148* (2013.01); *A61L 31/16* (2013.01); *A61L 2300/258* (2013.01); *A61L 2420/06* (2013.01); *C12N 2310/113* (2013.01); *C12N 2310/14* (2013.01); *C12N 2310/31* (2013.01); *C12N 2310/314* (2013.01); *C12N 2310/315* (2013.01); *C12N 2310/3125* (2013.01); *C12N 2310/3181* (2013.01); *C12N 2310/321* (2013.01); *C12N 2310/3231* (2013.01); *C12N 2310/3233* (2013.01); *C12N 2310/3341* (2013.01); *C12N 2310/351* (2013.01); *C12N 2310/3513* (2013.01); *C12N 2320/31* (2013.01)

(58) Field of Classification Search
CPC .................................................. C12N 15/113
See application file for complete search history.

(56) References Cited

U.S. PATENT DOCUMENTS

| 6,545,097 B2 | 4/2003 | Pinchuk |
|---|---|---|
| 2012/0059048 A1 | 3/2012 | Lavker |
| 2012/0259000 A1 | 10/2012 | Marionnet |

FOREIGN PATENT DOCUMENTS

| WO | 2009008720 | 1/2009 | |
|---|---|---|---|
| WO | 2010083464 | 7/2010 | |
| WO | WO-2013033165 A2 * | 3/2013 | ............. C12N 15/86 |

OTHER PUBLICATIONS

Boon et al., MicroRNA-29 in Aortic Dilation: Implications for Aneurysm Formation, Circ Res. 2011, 109:1115-1119.
Genbank: BC036201.1, *Homo sapiens* hypothetical protein LOC284801, mRNA (cDNA clone IMAGE:4830814), 2005.
Genbank: BC063704.1, *Homo sapiens* cDNA clone IMAGE:4804382, partial cds, 2003.
Kim et al., Prevention of Abdominal Aortic Aneurysm by Anti-MicroRNA-712 or Anti-MicroRNA-205 in Angiotensin II-Infused Mice, Arterioscler Thromb Vasc Biol. 2014;34:1412-1421.
Kumar et al. Role of flow-sensitive microRNAs in endothelial dysfunction and atherosclerosis—"Mechanosensitive Athero-miRs" Arterioscler Thromb Vasc Biol. 2014, 34(10): 2206-2216.
Kumar et al. Role of flow-sensitive microRNAs and long noncoding RNAs in vascular dysfunction and atherosclerosis, Vascul Pharmacol, 2019, 114: 76-92.

(Continued)

*Primary Examiner* — Ekaterina Poliakova-Georgantas
(74) *Attorney, Agent, or Firm* — Emory Patent Group

(57) ABSTRACT

This disclosure relates to methods and compositions for managing vascular conditions by targeting microRNA. In certain embodiments, the disclosure relates to antisense, RNA interference, and blocking oligonucleotide therapeutic compositions and uses related thereto.

21 Claims, 23 Drawing Sheets
Specification includes a Sequence Listing.

(56) References Cited

OTHER PUBLICATIONS

Maegdefessel et al. Inhibition of microRNA-29b reduces murine abdominal aortic aneurysm development, J Clin Invest. 2012, 122(2):497-506.
Mirbase, Stem-loop sequence hsa-mir-205, availiable at http://www.mirbase.org/cgi-bin/mima_entry_pl?acc=MI0000285, printed 2018.
Ni et al. MicroRNA-663 upregulated by oscillatory shear stress plays a role in inflammatory response of endothelial cells, Am J Physiol Heart Circ Physiol 300: H1762-H1769, 2011.
Siegwart et al. Combinatorial synthesis of chemically diverse core-shell nanoparticles for intracellular delivery, | PNAS, 2011, vol. 108, No. 32,12996-13001.
Son et al. The atypical mechanosensitive microRNA-712 derived from pre-ribosomal RNA induces endothelial inflammation and atherosclerosis, Nat Commun, 2013, 4:3000.

* cited by examiner

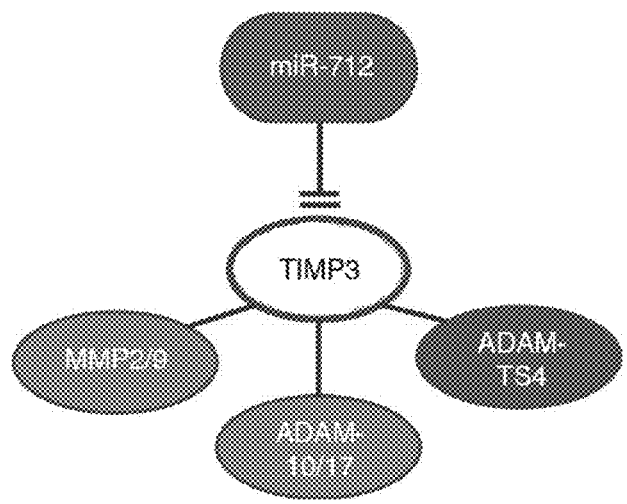
FIG. 3A
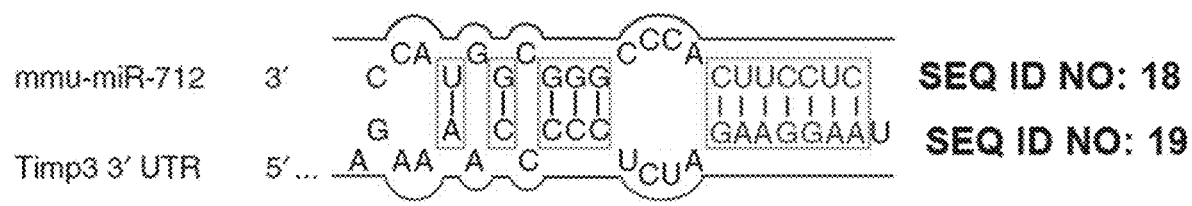
FIG. 3B
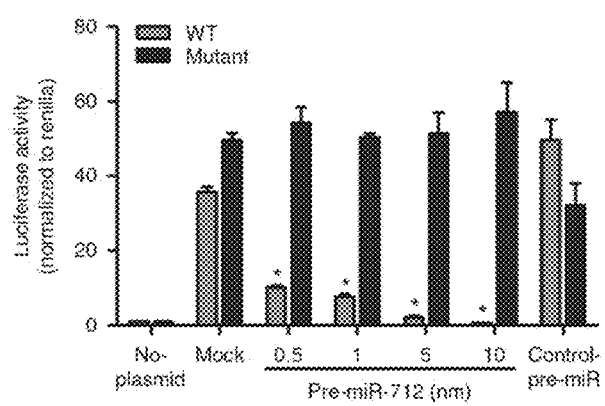 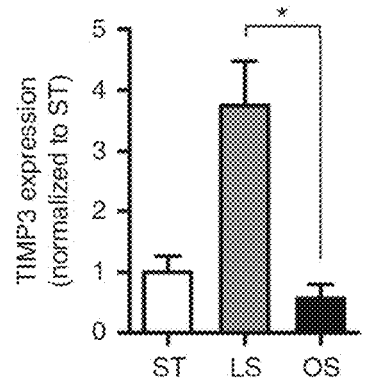
FIG. 3C　　　　　　　　　　FIG. 3D

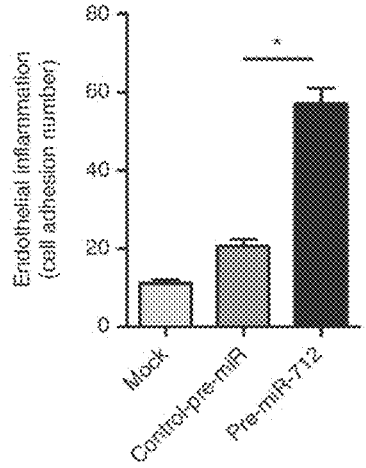
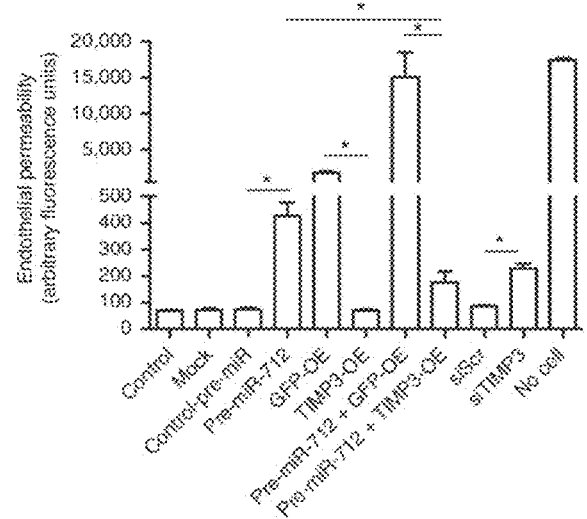
FIG. 4C
FIG. 4D
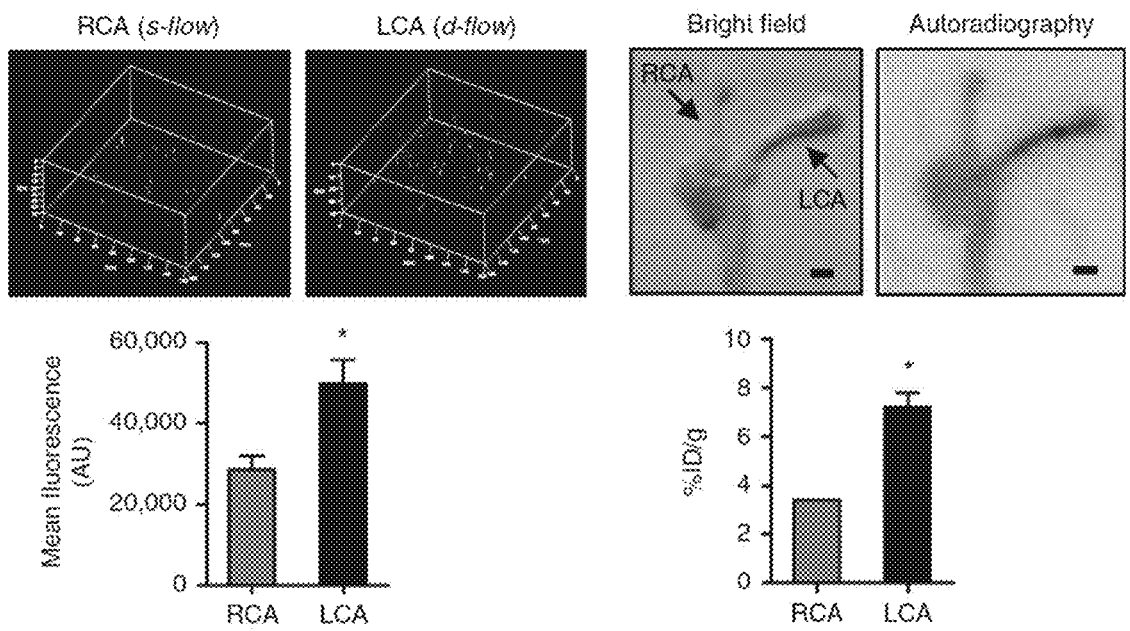
FIG. 5A
FIG. 5B

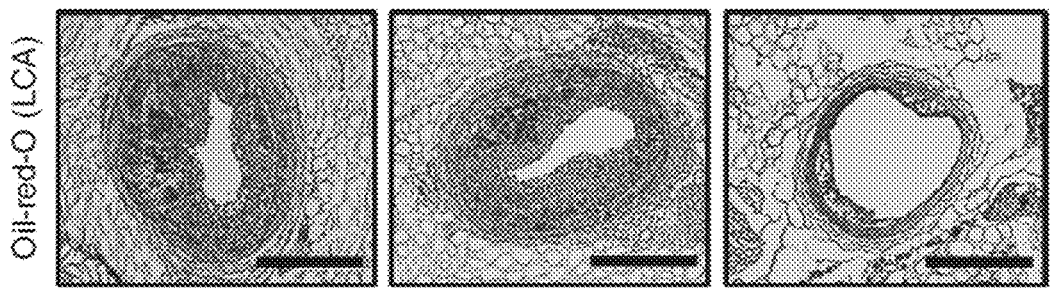
FIG. 6B
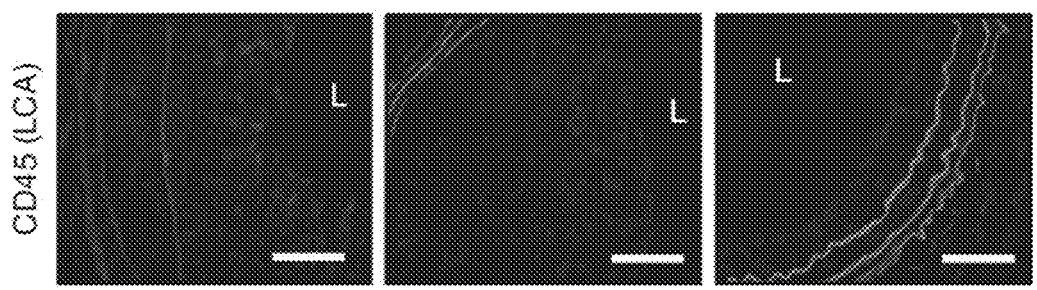
FIG. 6C
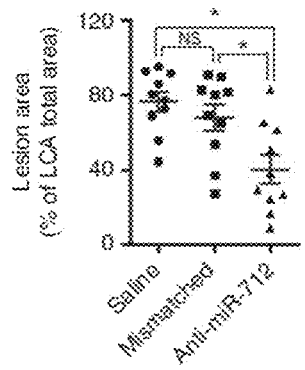 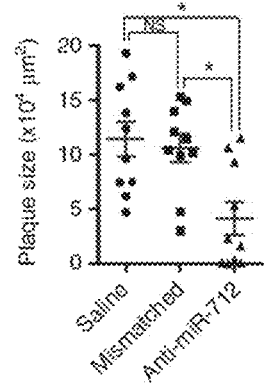
FIG. 6D                    FIG. 6E
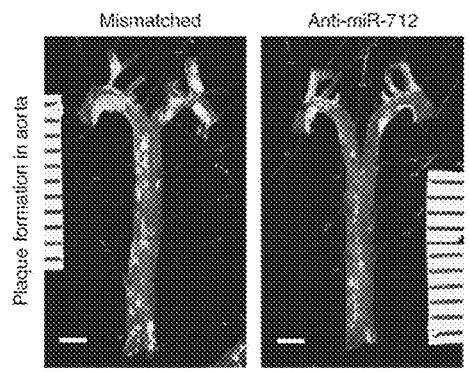 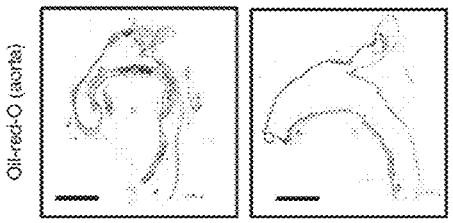
FIG. 6F                    FIG. 6G

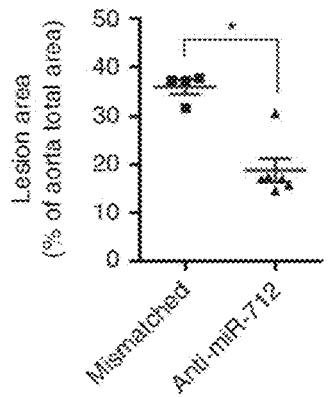
FIG. 6H
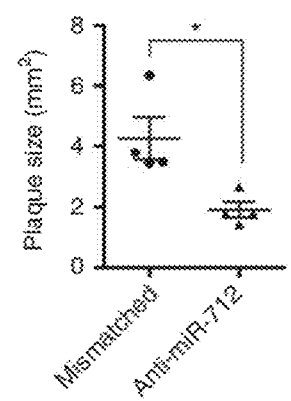
FIG. 6I
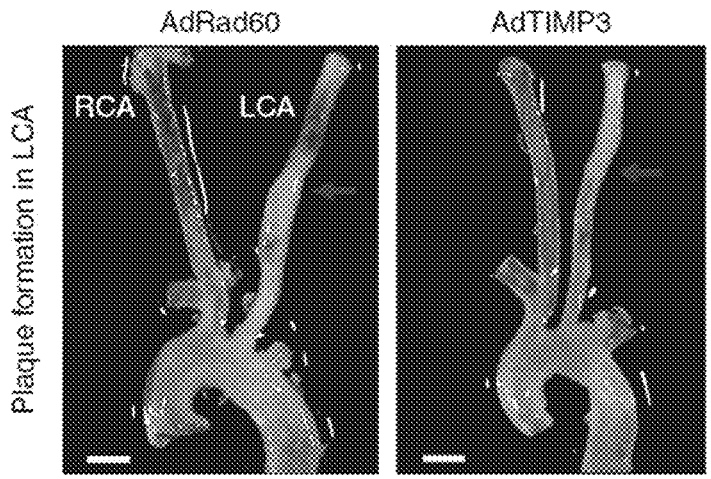
FIG. 6J
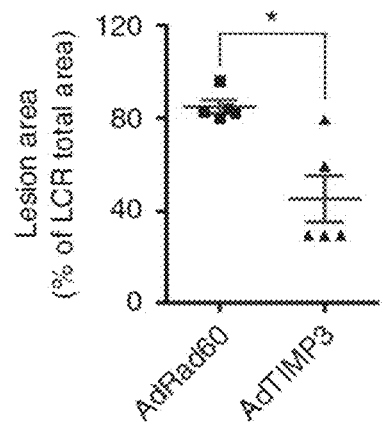
FIG. 6K
Seed sequence similarity between
miR-712 and miR-205
mmu-miR-712   5'-C UCCUUCACCCGGGCGGUACC-3'   SEQ ID NO: 18
mmu-miR-205   5'- UCCUUCAUUCCACCGGAGUCUG-3'   SEQ ID NO: 20
hsa-miR-205   5'- UCCUUCAUUCCACCGGAGUCUG-3'   SEQ ID NO: 21
FIG. 7A

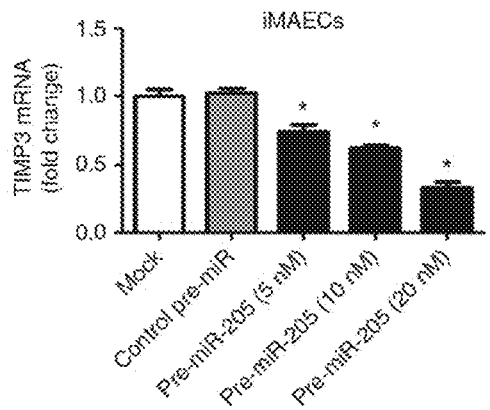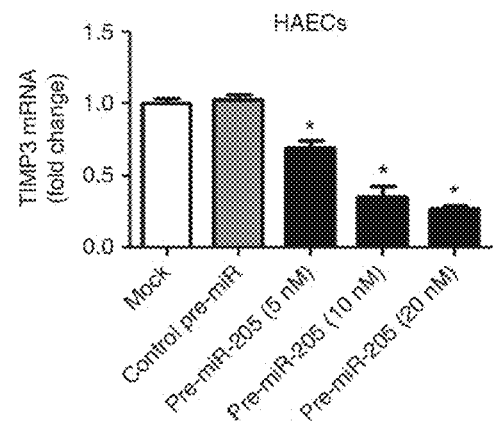
FIG. 7F  FIG. 7G
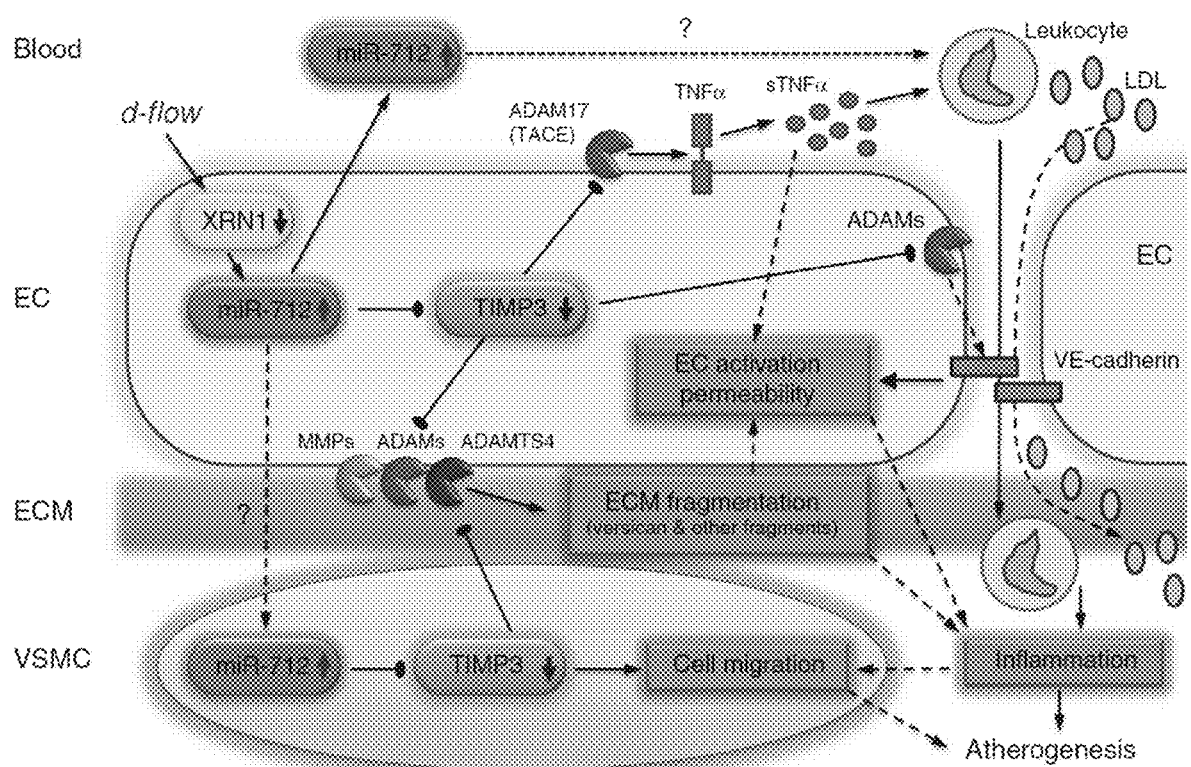
FIG. 8

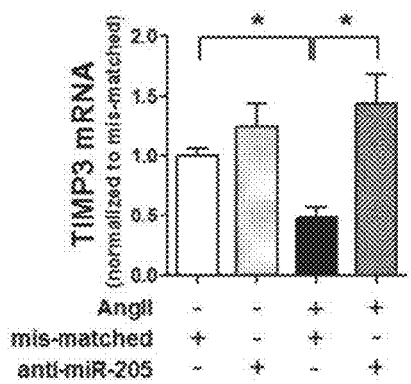 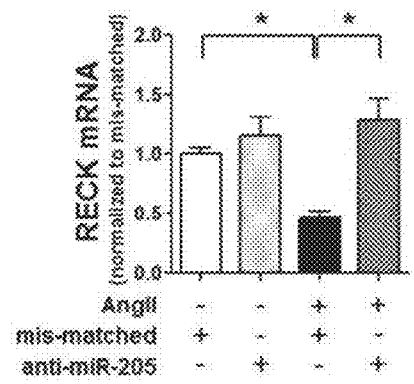
FIG. 13D    FIG. 13E
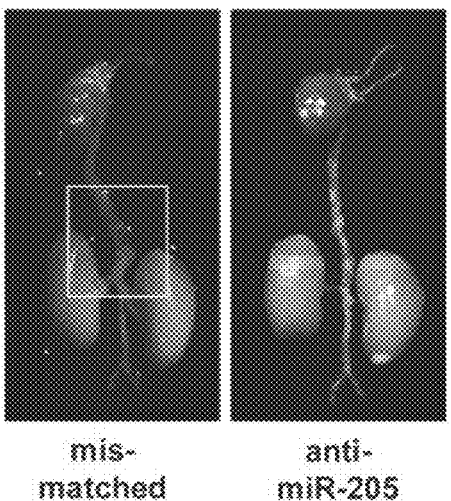
FIG. 14A
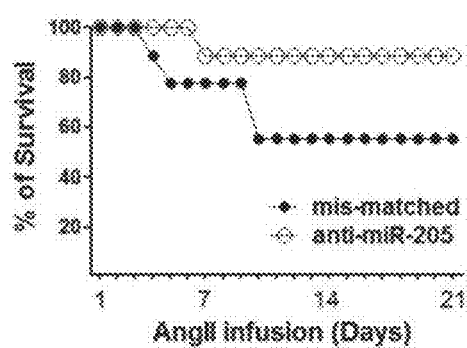 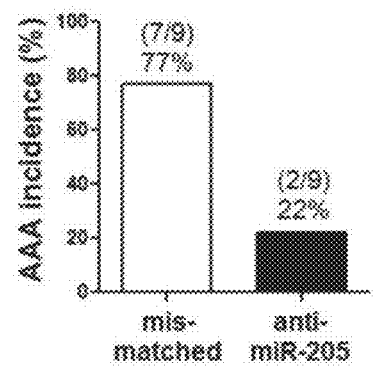
FIG. 14B    FIG. 14C

SEQUENCE LISTING

```
<160> NUMBER OF SEQ ID NOS: 21

<210> SEQ ID NO 1
<211> LENGTH: 93
<212> TYPE: RNA
<213> ORGANISM: Homo sapiens

<400> SEQUENCE: 1
ccuuccggcg ucccaggcgg ggcgccgcgg gaccgcccuc gugucugugg cggugggauc    60
ccgcggccgu guuuccugg uggcccggcc aug                                  93

<210> SEQ ID NO 2
<211> LENGTH: 93
<212> TYPE: RNA
<213> ORGANISM: Artificial
<220> FEATURE:
<223> OTHER INFORMATION: Synthetic

<400> SEQUENCE: 2
ccuuccggcg ucccaggcgg ggcgccgcgg gaccgcccuc gugucugugg cggugggauc    60
ccgcggccgu guuuccugg uggcccggcc aug                                  93

<210> SEQ ID NO 3
<211> LENGTH: 51
<212> TYPE: RNA
<213> ORGANISM: Artificial
<220> FEATURE:
<223> OTHER INFORMATION: Synthetic

<400> SEQUENCE: 3
ccuuccggcg ucccaggcgg ggcgccgcgg gaccgcccuc gugucugugg c              51

<210> SEQ ID NO 4
<211> LENGTH: 42
<212> TYPE: RNA
<213> ORGANISM: Artificial
<220> FEATURE:
<223> OTHER INFORMATION: Synthetic

<400> SEQUENCE: 4
ggugggaucc cgcggccgug uuuccuggu ggcccggcca ug                        42

<210> SEQ ID NO 5
<211> LENGTH: 36
<212> TYPE: RNA
<213> ORGANISM: Artificial
<220> FEATURE:
<223> OTHER INFORMATION: Synthetic

<400> SEQUENCE: 5
accgcccucg ugucugggc ggugggaucc cgcggc                               36

<210> SEQ ID NO 6
<211> LENGTH: 22
<212> TYPE: PRT
```

-continued

```
<213> ORGANISM: Artificial
<220> FEATURE:
<223> OTHER INFORMATION: Synthetic, x is 6-aminohexanoyl, B is
      beta-alanine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 6

Arg Xaa Arg Arg Asx Arg Arg Xaa Arg Ile Leu Phe Gln Tyr Arg Xaa
1               5                   10                  15

Arg Asx Arg Xaa Arg Asx
            20

<210> SEQ ID NO 7
<211> LENGTH: 22
<212> TYPE: PRT
<213> ORGANISM: Artificial
<220> FEATURE:
<223> OTHER INFORMATION: Synthetic, x is 6-aminohexanoyl, B is
      beta-alanine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 7

Arg Xaa Arg Arg Asx Arg Arg Xaa Arg Tyr Gln Phe Leu Ile Arg Xaa
1               5                   10                  15

Arg Asx Arg Xaa Arg Asx
            20

<210> SEQ ID NO 8
<211> LENGTH: 21
<212> TYPE: PRT
<213> ORGANISM: Artificial
<220> FEATURE:
<223> OTHER INFORMATION: Synthetic, x is 6-aminohexanoyl, B is
      beta-alanine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
```

```
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 8

Arg Xaa Arg Arg Asx Arg Arg Xaa Ile Leu Phe Arg Tyr Xaa Arg
1               5                   10                  15

Asx Arg Xaa Arg Asx
            20

<210> SEQ ID NO 9
<211> LENGTH: 15
<212> TYPE: DNA
<213> ORGANISM: Artificial
<220> FEATURE:
<223> OTHER INFORMATION: Synthetic

<400> SEQUENCE: 9
acgtctatac gccca                                                    15

<210> SEQ ID NO 10
<211> LENGTH: 19
<212> TYPE: DNA
<213> ORGANISM: Artificial
<220> FEATURE:
<223> OTHER INFORMATION: Synthetic

<400> SEQUENCE: 10
gtaccgcccg ggtgaagga                                                19

<210> SEQ ID NO 11
<211> LENGTH: 110
<212> TYPE: RNA
<213> ORGANISM: Homo sapiens

<400> SEQUENCE: 11
aaagauccuc agacaaucca ugugcuucuc uuguccuuca uuccaccgga gucugucuca    60
uacccaacca gauuucagug gagugaaguu caggaggcau ggagcugaca              110

<210> SEQ ID NO 12
<211> LENGTH: 16
<212> TYPE: DNA
<213> ORGANISM: Artificial
<220> FEATURE:
<223> OTHER INFORMATION: Synthetic

<400> SEQUENCE: 12
ccggtgguut guuggu                                                   16

<210> SEQ ID NO 13
<211> LENGTH: 27
<212> TYPE: DNA
<213> ORGANISM: Artificial
<220> FEATURE:
<223> OTHER INFORMATION: Synthetic

<400> SEQUENCE: 13
tccuctguuu tctggttggg tutgugu                                       27

<210> SEQ ID NO 14
<211> LENGTH: 22
```

```
<212> TYPE: DNA
<213> ORGANISM: Artificial
<220> FEATURE:
<223> OTHER INFORMATION: Synthetic

<400> SEQUENCE: 14
cuguctccgg tgguutguug gu                                              22

<210> SEQ ID NO 15
<211> LENGTH: 45
<212> TYPE: DNA
<213> ORGANISM: Artificial
<220> FEATURE:
<223> OTHER INFORMATION: Synthetic

<400> SEQUENCE: 15
cugctccutg cctcctguuc ttcuctccuc tguuutctgg ttggg                     45

<210> SEQ ID NO 16
<211> LENGTH: 14
<212> TYPE: DNA
<213> ORGANISM: Artificial
<220> FEATURE:
<223> OTHER INFORMATION: Synthetic

<400> SEQUENCE: 16
cgcccgggtg aaga                                                       14

<210> SEQ ID NO 17
<211> LENGTH: 20
<212> TYPE: DNA
<213> ORGANISM: Artificial
<220> FEATURE:
<223> OTHER INFORMATION: Synthetic

<400> SEQUENCE: 17
gcctcctgaa cttcactcca                                                 20

<210> SEQ ID NO 18
<211> LENGTH: 21
<212> TYPE: RNA
<213> ORGANISM: Mus musculus

<400> SEQUENCE: 18
cuccuucacc cgggcgguac c                                               21

<210> SEQ ID NO 19
<211> LENGTH: 22
<212> TYPE: RNA
<213> ORGANISM: Mus musculus

<400> SEQUENCE: 19
agaaaacccc cucagaagga au                                              22

<210> SEQ ID NO 20
<211> LENGTH: 22
<212> TYPE: RNA
<213> ORGANISM: Mus musculus

<400> SEQUENCE: 20
uccuucauuc caccggaguc ug                                              22

<210> SEQ ID NO 21
<211> LENGTH: 22
<212> TYPE: RNA
```

```
<213> ORGANISM: Homo sapiens

<400> SEQUENCE: 21
uccuucauuc caccggaguc ug                                              22
```

METHODS AND COMPOSITIONS FOR MANAGING VASCULAR CONDITIONS

CROSS-REFERENCE TO RELATED APPLICATIONS

This application is a division of U.S. patent application Ser. No. 16/107,936 filed Aug. 21, 2018, which is a continuation of U.S. patent application Ser. No. 14/772,978 filed Sep. 4, 2015, which is the National Stage of International Application No. PCT/US2014/023396 filed Mar. 11, 2014, which claims the benefit of priority to U.S. Provisional Application No. 61/776,201 filed Mar. 11, 2013, U.S. Provisional Application No. 61/904,026 filed Nov. 14, 2013, and U.S. Provisional Application No. 61/916,449 filed Dec. 16, 2013. The entirety of each of these applications is hereby incorporated by reference for all purposes.

STATEMENT REGARDING FEDERALLY FUNDED RESEARCH

This invention was made with government support under HL075209 and HL080711 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 11236USDIV_ST25.txt. The text file is 6 KB, was created on Dec. 3, 2019, and is being submitted electronically via EFS-Web.

BACKGROUND

Atherosclerosis, i.e., hardening of the arteries, occurs when substances such as fat and cholesterol build up in the walls of arteries and form plaques. Plaque buildup narrows arteries, also referred to as stenosis, making them stiffer and more difficult for blood to flow. Pieces of plaque often break off forming an embolism blocking blood flow resulting in tissue damage which is a common cause of heart attacks and stroke. Carotid endarterectomy (CEA) is a surgical procedure used to prevent stroke, by correcting stenosis in the common carotid artery. Other procedures include endovascular angioplasty and stenting. Surgical procedures are expensive and undesirable. In addition, post-operative incidences of heart attack, stroke, and death are significant. Thus, there is a need for improved methods for treating and preventing atherosclerosis.

Atherosclerosis preferentially occurs in arterial regions exposed to disturbed flow (d-flow), in part, due to alterations in gene expression. Vascular endothelial cells respond to blood flow through mechanosensors, which transduce the mechanical force associated with flow (known as shear stress) into cell signaling events and ultimately bring about changes in gene expression. Disturbed-flow promotes while stable-flow inhibits atherogenesis, respectively, through differential regulation of pro-atherogenic and atheroprotective genes.

Ni et al. report the discovery of mechanosensitive genes in vivo using mouse carotid artery endothelium exposed to disturbed flow. Blood, 2010, 116(15): e66-73. Boon et al. report MicroRNA-29 in Aortic Dilation. Circ Res, 2011; 109:1115-1119. Maegdefessel et al. report inhibition of microRNA-29b reduces murine abdominal aortic aneurysm development. J Clin Invest, 2012, 122(2):497-506.

Son et al. report the atypical mechanosensitive microRNA-712 derived from pre-ribosomal RNA by an XRN1-dependent manner induces endothelial inflammation and atherosclerosis. Nature Comm. 2013, 4:3000.

Reference cited herein are not an admission of prior art.

SUMMARY

This disclosure relates to methods and compositions for managing vascular conditions by targeting microRNA. In certain embodiments, the disclosure relates to antisense, blocking oligonucleotides, and RNA interference therapeutic compositions and uses related thereto.

In certain embodiments, the disclosure relates to compositions comprising isolated nucleobase polymers that binds or hybridizes any miRNA disclosed herein, e.g., human miR-21, miR-133b, miR-378 and miR-205, for any of the uses disclosed herein.

In certain embodiments, the disclosure relates to composition comprising an isolated nucleobase polymer that binds RNA of miR-205 (SEQ ID NO: 11) AAAGAUCCUCA-GACA AUCCAUGUGCUUCUCUUGUCCUUCAUUC-CACCGGAGUCUGUCUCAUACCCAACCA GAUUUCAGUGGAGUGAAGUUCAGGAGGCAUG-GAGCUGACA. Typically, the nucleobase polymer is a nucleic acid or nucleic acid mimetic that hybridizes to miR-205 (SEQ ID NO: 11).

In certain embodiments, the disclosure relates to composition comprising an isolated nucleobase polymer that binds RNA of miR-663 (SEQ ID NO: 1) CCUUCCGGCGU-CCCAGGCGGGGCGCCGCGGGACCGCCCUCGUGU-CUGUGGCGGUG GGAUCCCGCGGCCGUGUUUUC-CUGGUGGCCCGGCCAUG. Typically, the nucleobase polymer is a nucleic acid or nucleic acid mimetic that hybridizes to miR-663 (SEQ ID NO: 1).

In certain embodiments, a nucleobase polymer disclosed herein comprises monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl)morpholino) (piperazin-1-yl)phosphinate, or peptide nucleic acids or combinations thereof.

In certain embodiments, a nucleobase polymer disclosed herein is 3' or 5' terminally conjugated to a polyphosphate, polyphosphate ester, hydrocarbon, polyethylene glycol, saccharide, polysaccharide, cell penetrating peptide or combinations thereof. Typically, the cells penetrating peptide is a positively charged peptide, arginine-rich peptide, oligoarginine peptide (7-12), or octa-arginine (R8).

In certain embodiments, a nucleobase polymer disclosed herein comprises 8, 9, 10, 15, 20, 25, 30, 40, 50, 60, 70, 80, 90 or more nucleobases. In certain embodiments, a nucleobase polymer disclosed herein comprises 8, 9, 10, 15, 20, 25, 30, 40, 50, 60, 70, 80, 90 or more continuous nucleobases that hybridize SEQ ID NO:1 or SEQ ID NO:11.

In certain embodiments, a nucleobase polymer disclosed herein is the reverse complement of SEQ ID NO:1 or SEQ ID NO:11 has greater than 60%, 70%, 80%, 90%, 95% or more sequence identity over a 20, 30, 40, 50, 60, 70, 80, or more nucleobase comparison window.

Typically, a nucleobase polymer is less than 100 or 50 nucleobases.

In certain embodiments, the disclosure relates to particles comprising a cyclodextrin polymer or a particle with a lipid, or hydrophilic membrane and ionizable or cationic core comprising a nucleobase polymer disclosed herein.

In certain embodiments, this disclosure relates to pharmaceutical compositions comprising the nucleobase polymer disclosed herein or a particle comprising a nucleobase polymer disclosed herein, and a pharmaceutically acceptable excipient.

In certain embodiments, the disclosure relates to methods of treating or preventing a vascular disease or condition comprising administering an effective amount of a pharmaceutical composition disclosed herein to a subject in need thereof.

In certain embodiments, the subject is a human that is at risk of, exhibiting symptoms of, or diagnosed with atherosclerosis, aneurysm, peripheral vascular disease, coronary heart disease, heart failure, right ventricular hypertrophy, cardiac dysrhythmia, endocarditis, inflammatory cardiomegaly, myocarditis, vascular heart disease, stroke, cerebrovascular disease, or peripheral arterial disease, or cancer.

In certain embodiments, the subject has type I or type II diabetes, impaired glucose tolerance, elevated serum C-reactive protein concentration, vitamin B6 deficiency, dietary iodine deficiency, hypothyroidism, hyperlipidemia, hypertension, or is older than 50 years old, or smokes cigarettes daily.

In certain embodiments, the pharmaceutical composition is administered in combination with a statin, atorvastatin, cerivastatin, fluvastatin, lovastatin, mevastatin, pitavastatin, pravastatin, rosuvastatin, simvastatin, ezetimibe, amlodipine, niacin, aspirin, omega-3 fatty acid, or combinations thereof.

In certain embodiments, the disclosure relates to compositions comprising a double stranded RNA consisting of between 15 and 30 continuous nucleotides of SEQ ID NO:1 or SEQ ID NO:11. In certain embodiments, the double stranded RNA is 3' end capped with one or more thymidine nucleotides and/or the passenger strand of the RNA comprises 5' end polyphosphate.

In certain embodiments, the disclosure relates to particles comprising a lipid membrane and ionizable or cationic core comprising the double stranded RNA disclosed herein.

In certain embodiments, the disclosure relates to pharmaceutical composition comprising the RNA disclosed herein or a particle comprising RNA disclosed herein, and a pharmaceutically acceptable excipient.

In certain embodiments, the disclosure relates to methods of treating or preventing a vascular disease condition comprising administering an effective amount of a pharmaceutical composition comprising an RNA disclosed herein or a particle comprising RNA disclosed herein.

In certain embodiments, the disclosure relates to methods for inhibiting or preventing atherosclerosis, aortic aneurysm, rheumatoid arthritis and cancer in human patients by treating them with using an effective amount of a compound that inhibits miR-205/miR-712/miR-663 family, which in turn increases or preserves expression of tissue inhibitor of metalloproteinase-3 (TIMP3) and agents that increase or preserve the expression of XRN1 upregulation, and reversion-inducing cysteine-rich protein with Kazal motifs (RECK), wherein said compound is selected from the group consisting of microRNA inhibitors of miR-712/miR-205/miR-663 family by using nucleic acid sequences that complement the whole or a part of the miRNA sequence such as the seeding sequence. The nucleic acid inhibitors can be synthesized by using locked nucleic acid (LNA)-based designs.

In certain embodiments, the disclosure relates to methods comprising administering an effective amount of a microRNA-712/miR-205/miR-663 antagonist (anti-miR-712, anti-miR-205, or anti-miR-663) to the diseased tissues and cell types.

In certain embodiments, the disclosure relates to medical devices, such as stents, e.g., mesh tube comprising compositions disclosed herein, e.g., recombinant human TIMP3 and RECK, antisense nucleobase polymers, blocking oligonucleotide, gene therapy vectors, anti-miR-205, anti-miR-712, anti-miR-663 or their derivatives, and RNA interference therapeutic compositions.

In certain embodiments, the disclosure relates to vascular or non-vascular medical device coated or conjugated with the inhibitor of miR-205, miR-712, or miR-663. In certain embodiments, the inhibitors are linked to polymers on the surface of the device. In certain embodiments, the inhibitor is integrated to release with biodegradable polymer. In certain embodiments, medical device is selected from a stents, pace maker, guide wire, delivery balloon, catheter, bioresorbable vascular scaffold, embolic protection device. In certain embodiments, the inhibitor is a nucleobase polymer.

In certain embodiments, the disclosure relates to a gene therapy using a vector that expresses human TIMP3 or RECK in human cells.

BRIEF DESCRIPTION OF THE DRAWINGS

FIG. 3A shows TIMP3 as a potential target of miR-712 and its link to putative downstream metalloproteinase targets.

FIG. 3B shows the seed sequence of miR-712 (SEQ ID NO: 18) and complementary 30-UTR sequence of TIMP3 (SEQ ID NO: 19).

FIG. 3C shows data where iMAECs transfected with dual luciferase reporter plasmids containing wild-type (WT) or mutant TIMP3-30-UTR were treated with pre-miR-712 or control pre-miR. Firefly luciferase activity (normalized to control Renilla luciferase) indicating TIMP3 expression was determined using Luc-Pair miR Luciferase Assay Kit (n=3 each, data shown as mean±s.e.m.; *p<0.05 as determined by Student's t-test).

FIG. 3D shows data where TIMP3 expression in iMAECs determined by qPCR was decreased by exposure to OS compared with LS or ST for 24 h (n=6, data shown as mean±s.e.m.; *P<0.05 as determined by Student's t-test).

FIG. 4C shows data where iMAECs were transfected with pre-miR-712 (20 nM) or control and leukocyte adhesion assay was performed using $2.5 \times 10^5$ fluorescent-labelled J774.4 mouse monocyte cells. Adherent cells were counted (n=5 independent experiments, data shown as mean±s.e.m.; *p<0.05 as determined by one-way ANOVA).

FIG. 4D shows data where iMAECs were transfected with TIMP3-OE or its GFP vector control (GFP-OE), TIMP3 or scrambled control siRNA (siTIMP3 or siScr, 150 nM), pre-miR-712 or control pre-miR (20 nM), pre-miR-712 with GFP-OE or TIMP3-OE, and no treatment (control), transfection (mock) or no cell controls for 24 h. Cells were then exposed to static, LS or OS for 24 h, and endothelial permeability was determined using a FITC-dextran-based in vitro vascular permeability kit (Cultrex). Fluorescence signals from FITC-dextran in the lower chamber were quantified and plotted as arbitrary fluorescence units (n=3 each from two independent experiments, data shown as mean±s.e.m.; *p<0.05 as determined by one-way ANOVA).

FIG. 5A shows data where TexRed-615-labelled control anti-miR or saline was injected (s.c.) in C57B16 mice. Carotid arteries were dissected out 24 h later, and using Zeiss 510 confocal microscope z-stack images of the en face sections were obtained. Images were rendered to three dimensions, bounding box was drawn on the area of interest and scaled coordinate axes were drawn and fluorescence signals from Red channel were processed and quantified. Graph shows mean fluorescence intensity of TexRed-615 signals from carotids (n=5, data shown as mean±s.e.m.).

FIG. 5B shows data where following partial carotid ligation and HFD for 2 weeks, ApoE$^{-/-}$ mice were injected with $^{64}$Cu-labelled antimiR-712 via tail vein. After 3 h, aortic trees including carotids were prepared and autoradiographed, which was used to quantitate percentage of injected dose per gram (n=6, data shown as mean±s.e.m.; *p<0.05 as determined by Student's t-test). Scale bar, 1 mm.

FIG. 6B shows frozen sections prepared from the middle parts of these arteries, denoted by arrows stained with Oil-Red-O and plaque size was quantified (n=10 each, data shown as mean±s.e.m.; *p<0.05 as determined by one-way ANOVA). Scale bar, 200 mm.

FIG. 6C shows representative confocal imaging of frozen sections immunostained with CD45 antibody is shown (n=10). Scale bar, 20 μm. For chronic study, ApoE$^{-/-}$ mice were fed western diet (without any partial ligation surgery) and were treated with anti-miR-712 (5 mgkg$^{-1}$, twice a week, s.c.) or mismatched control for 3 months (n=10 each). (f) Aortic trees were dissected and examined by en face Oil-Red-O staining and the lesion area was quantified (n=4-6 in each group, data shown as mean±s.e.m.; *p<0.05 as determined by Student's t-test). Scale bar, 2 mm.

FIG. 6D shows quantified data as in FIG. 6A.

FIG. 6E shows quantified data as in FIG. 6B.

FIG. 6H shows quantified data as in FIG. 6C.

FIG. 6F shows data where aortic arches were longitudinally sectioned

FIG. 6G shows data where stained with Oil-Red-O and plaque size was quantified (n=4 each, data shown as mean±s.e.m.; *p<0.05 as determined by Student's t-test). Scale bar, 2 μm.

FIG. 6I shows quantified data in FIG. 6G.

FIG. 6J shows data for TIMP3 overexpression, ApoE$^{-/-}$ mice were injected once with AdTIMP3 (10$^8$ p.f.u. per animal, via tail vein) or control virus (RAD60, 10$^8$ p.f.u. per animal) 5 days before partial carotid ligation and high-fat diet for 2 weeks. Aortic trees including the carotids were dissected and examined by bright field imaging and lesion area was quantified (n=5, data shown as mean±s.e.m.; *p<0.05 as determined by Student's t-test). Scale bar, 1 mm.

FIG. 6K shows quantified data in FIG. 6J.

FIG. 7A illustrates seed sequence similarity where highlighted region shows the seed sequence match between the murine miR-712 (SEQ ID NO: 18) and murine (SEQ ID NO: 20) and human miR-205 (SEQ ID NO: 21), and those shown indicate additional conserved sequences.

FIG. 7F shows data where expression of TIMP3 was determined by qPCR in iMAECs transfected with increasing concentrations of pre-miR-205 or control pre-miR compared with vehicle controls (mock) (n=3; data shown as means±s.e.m.; *p<0.05 as determined by Student's t-test).

FIG. 7G shows data for HAECs.

FIG. 8 illustrates a working hypothesis that miR-712 induces inflammation and atherosclerosis by targeting TIMP3; however, it is not intended that embodiment of this disclosure be limited by any particular mechanism. D-flow stimulates miR-712 expression in endothelium by an XRN1-dependent mechanism. Increased miR-712 stimulates endothelial inflammation, permeability and extracellular matrix (ECM) fragmentation by downregulating TIMP3, which is a critical inhibitor of matrix metalloproteinases (MMPs and ADAMs). Decreased TIMP3 expression by miR-712 induces inflammation and atherosclerosis by activating a multitude of metalloproteinases: (1) ADAM17/TACE that releases soluble-TNFα that may induce local and systemic inflammation; (2) ADAMs that shed junctional VE-cadherin, increasing permeability that facilitates LDL and leukocyte infiltration; (3) ADAMTS leading to versican fragmentation; and (4) MMPs leading to ECM degradation leading to vessel wall remodeling. In addition, miR-712 expression is also increased in whole blood and vascular smooth muscle cells (VSMCs) suggesting either transfer of miR-712 from endothelium to these compartments or increase in its local production in these compartments. Increased miR-712 in VSMCs induces their migration while circulating miR-712 may affect blood leukocytes further contributing to atherogenesis.

FIG. 13D shows data for TIMP3.

FIG. 13E shows data for RECK.

FIG. 14A shows photographs showing macroscopic features of aneurysms induced by AngII. ApoE$^{-/-}$ mice treated with anti-miR-205 or mis-matched control (5 mg/kg) were infused with AngII for 3 weeks. The square shows typical AAAs in ApoE$^{-/-}$ mice.

FIG. 14B shows data on the survival rate of AngII-induced AAA in anti-mR-205 treated group compared to mis-matched controls are shown.

FIG. 14C shows data on the incidence.

DETAILED DISCUSSION

Figure 1A:
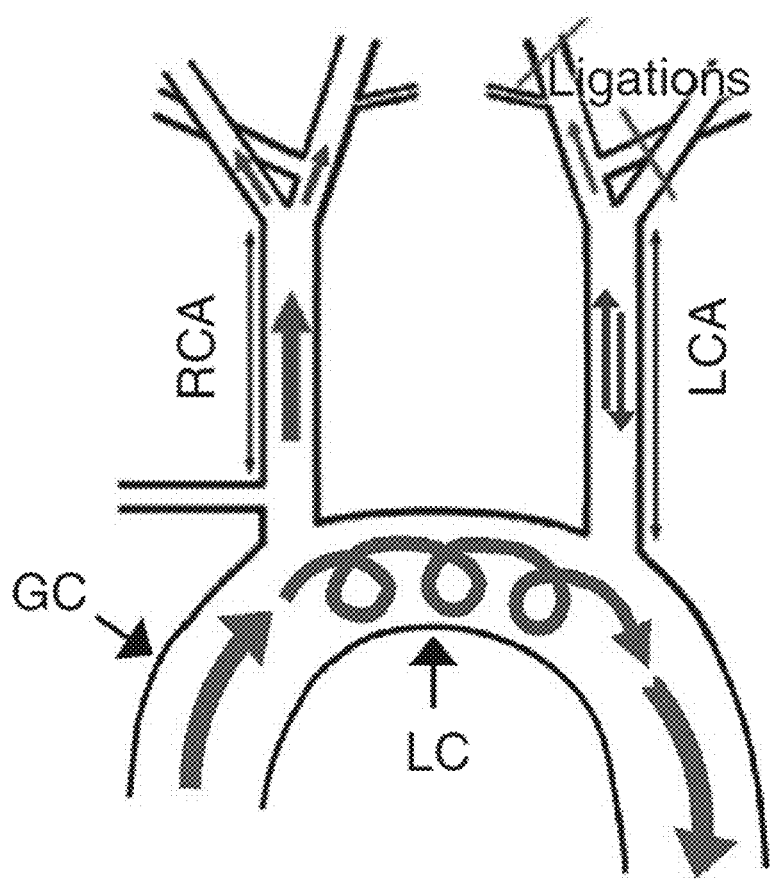
FIG. 1A shows a scheme of naturally occurring d-flow (lesser curvature, LC) and stable flow (s-flow) regions (greater curvature, GC) in the aortic arch. Also shown is the surgically induced d-flow in partial carotid ligation model in which three of the four caudal branches of the left common carotid artery (LCA) are ligated, while the contralateral right common carotid artery (RCA) remains untouched as an internal control.
Figure 1B:
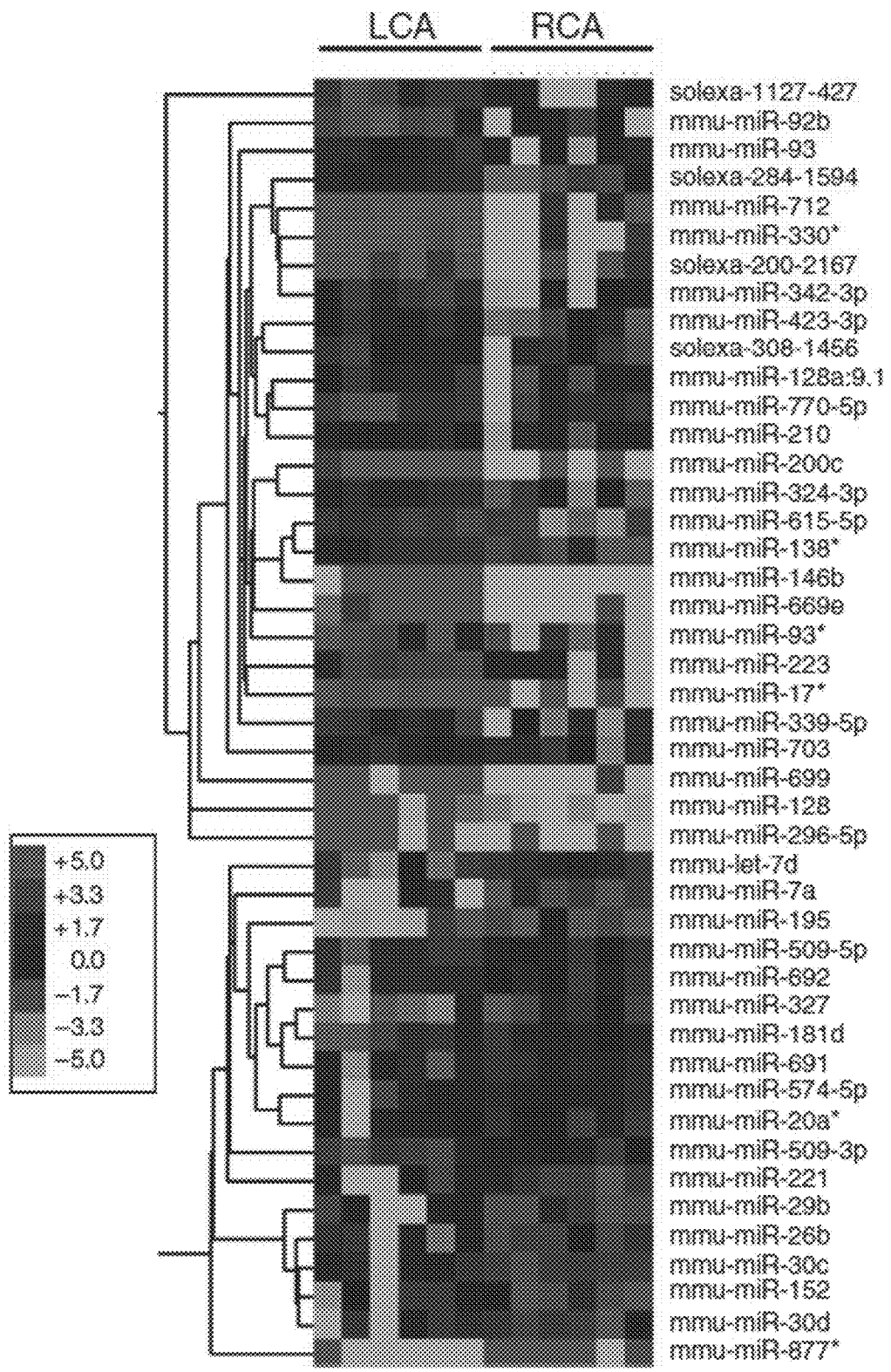
FIG. 1B shows data on endothelial-enriched total RNAs obtained from intima of mouse (C57BL/6) left carotid (flow-disturbed LCA) and right carotid (contralateral control, RCA) at 48 h post ligation were analyzed by gene array (Illumina Bead Chip). Hierarchical clustering analyses of mechanosensitive miRNAs found in LCA endothelium compared with that of RCA are shown as heat maps. The expression levels are continuously mapped on the color scale provided at the top of the figure. Each column represents a single sample pooled from three different LCAs or RCAs, and each row represents a single miRNA probe (n=3).
Figure 1C:
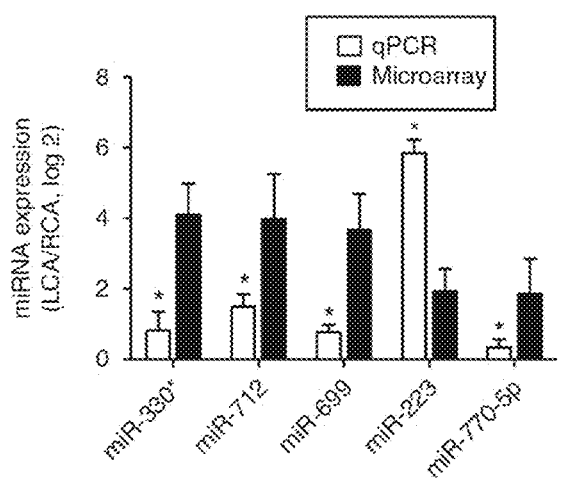
FIG. 1C shows data on validation of miRNA microarray results by qPCR. Quantitative PCR (qPCR), using additional independent RNA samples, was used to validate the above miRNA array data. Ten miRNAs (five up-, five downregulated miRNAs at 48 h post ligation) were selected based on fold change by flow. The qPCR study validated the microarray results for five upregulated (miR-712, -330*, -699, -223 and 770-5p).
Figure 1D:
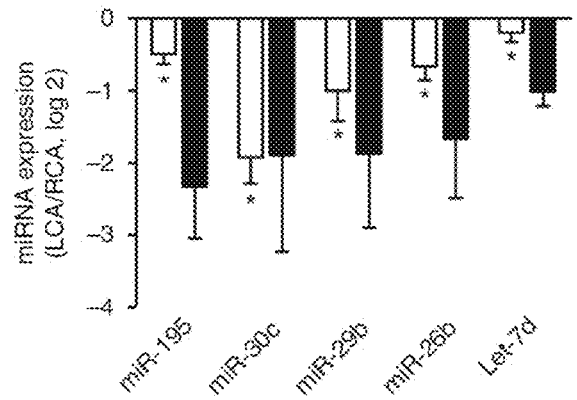
FIG. 1D shows data on five downregulated (miR-195, -30c, -29b, -26band let-7d) miRNAs at the 48 h time point (n=5 each, data shown as mean±s.e.m.; *P<0.05 as determined by paired t-test).
Figure 1E:
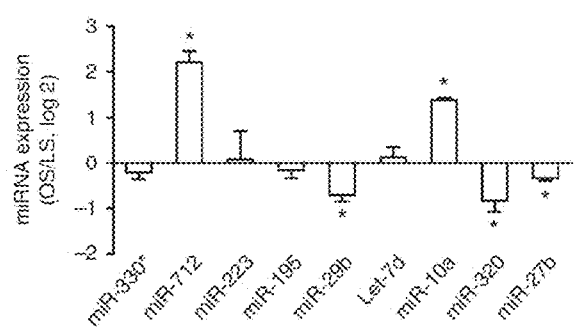
FIG. 1E shows data. To further validate whether the mechanosensitive miRNAs that were identified in vivo responded specifically to shear stress, expression of these miRNAs were tested in vitro using iMAECs that were subjected to LS or OS, mimicking s-flow and d-flow in vitro, respectively. Among the nine different miRNAs examined, seven miRNAs were differentially expressed under OS (n=6 each, data shown as mean±s.e.m.; *P<0.05 as determined by paired t-test). These results showed that miR-712 was the most consistently and robustly upregulated miRNA both in vivo and under d-flow conditions in vitro.
Figure 2A:
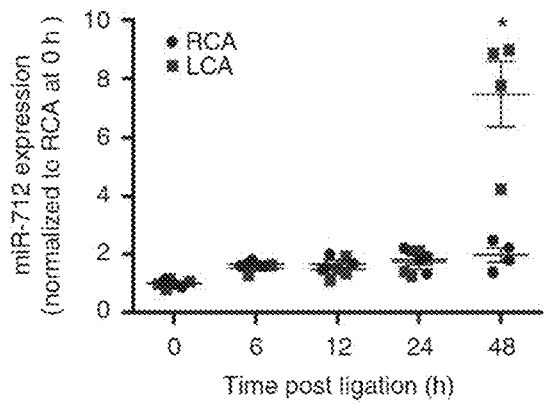
FIG. 2A shows data where expression of miR-712 was determined by qPCR using endothelial-enriched RNA obtained from LCA and RCA following partial carotid ligation in C57B16 mouse (0-48 h) (n=4, data shown as mean±s.e.m.; *P<0.05 as determined by paired t-test).
Figure 2B:
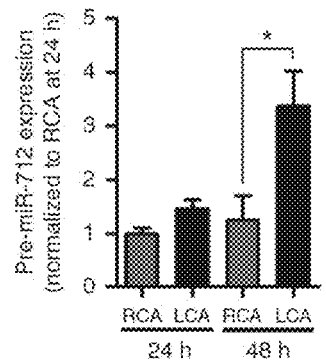
FIG. 2B shows data where expression of pre-miR-712 by d-flow in LCA and RCA endothelium following partial ligation at 24 and 48 h was quantitated by miScript miRNA qPCR assay (n=8 each; *p<0.05 as determined by Student's t-test).
Figure 2C:
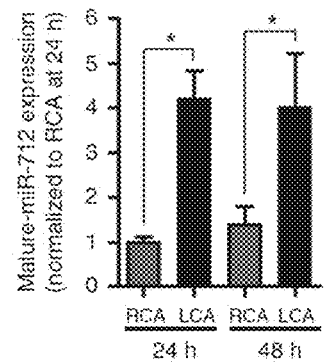
FIG. 2C shows data on expression of mature miR-712.
Figure 2D:
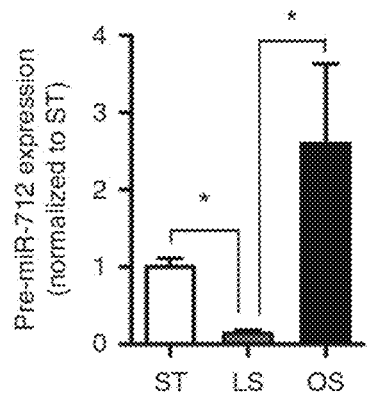
FIG. 2D shows data were expression of pre-miR-712 was measured by miScript miRNA qPCR in iMAECs exposed to laminar (LS), oscillatory shear (OS) or static (ST) for 24 h (n=6, data shown as mean±s.e.m.; *p<0.05 as determined by Student's t-test).
Figure 2E:
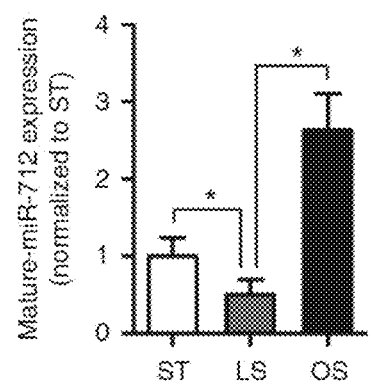
FIG. 2E shows data on mature miR-712.
Figure 2F:
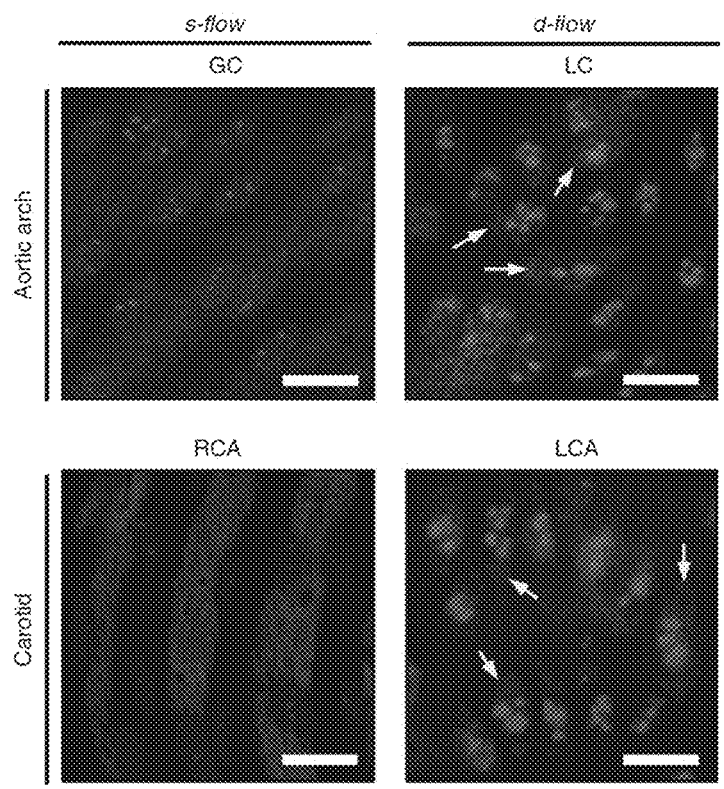
FIG. 2F shows data where aortic arch (LC and GC) and LCA and RCA obtained at 2 days post ligation from C57B16 mice were subjected to fluorescence in situ hybridization using DIG-labelled miR-712 probe and anti-DIG antibody, which was detected by tyramide signal amplification method using Cy3 and confocal microscopy, (n=6). DAPI nuclear stain; autofluorescent elastic lamina; arrows indicate cytosolic miR-712 expression. scale bars, 20 mm.
Figure 2G:
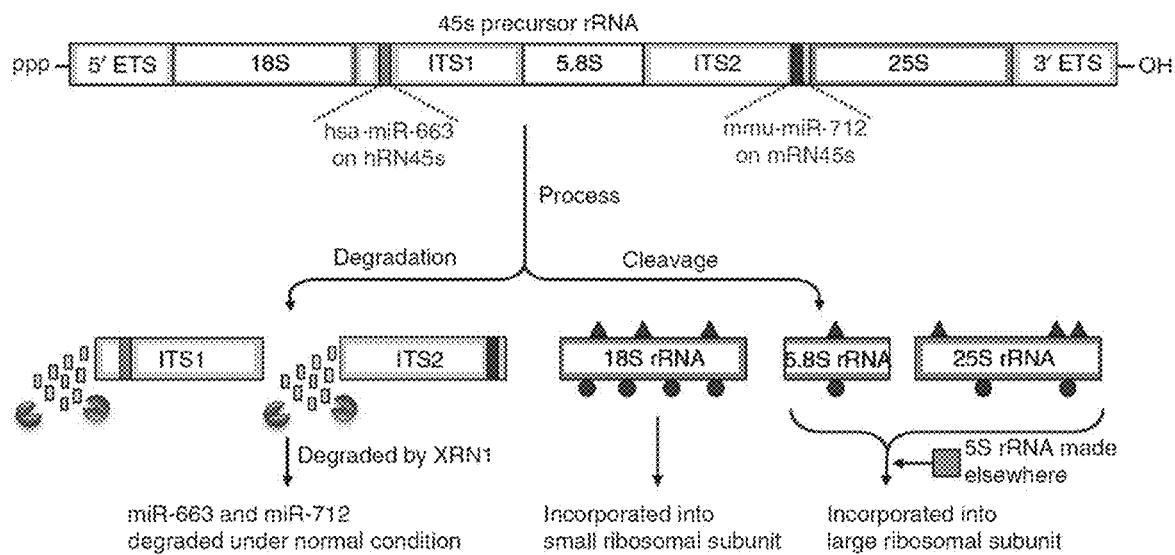
FIG. 2G shows the potential structure and processing of pre-ribosomal RNA gene, RN45s, which is composed of 18S, 5.8S and 28S rRNA sequences with two intervening spacers ITS1 and ITS2. The sequences matching murine miR-712 in ITS2 and its putative human counterpart miR-663 in ITS1 are indicated as well.
Figure 2H:
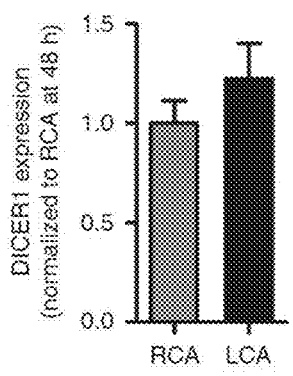
FIG. 2H shows data where expression of DICER in mouse RCA and LCA (2 days post ligation) was determined by qPCR (n=4, data shown as mean±s.e.m.; *p<0.05 as determined by paired ttest).
Figure 2I:
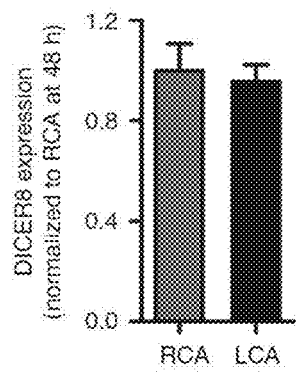
FIG. 2I shows data for DGCR8.
Figure 2J:
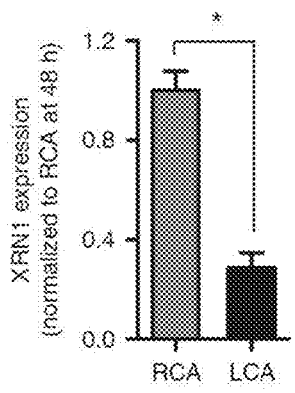
FIG. 2J shows data for XRN1.
Figure 2K:
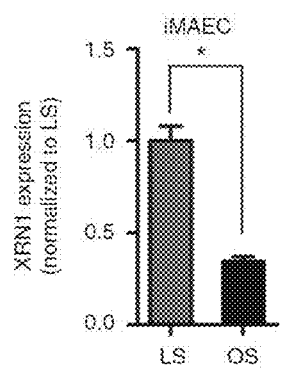
FIG. 2K shows data where XRN1 expression in iMAECs exposed to LS or OS for 24 h was determined by qPCR (n=3 each, data shown as mean±s.e.m.; *p<0.05 as determined by Student's t-test).
Figure 2L:
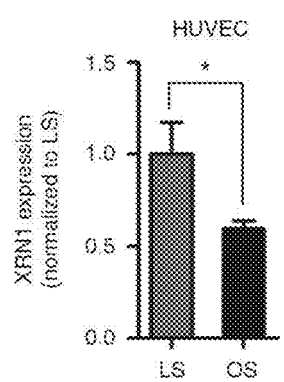
FIG. 2L shows data for HUVECs.
Figure 2M:
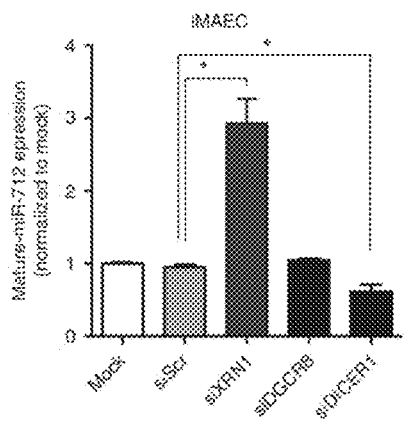
FIG. 2M shows data whereimiR-712 expression was induced by treating iMAECs with XRN1 siRNA but not by DGCR8 siRNA and DICER1 siRNA (n=3 each, data shown as mean±s.e.m.; *p<0.05 as determined by Student's t-test).
Figure 3E:
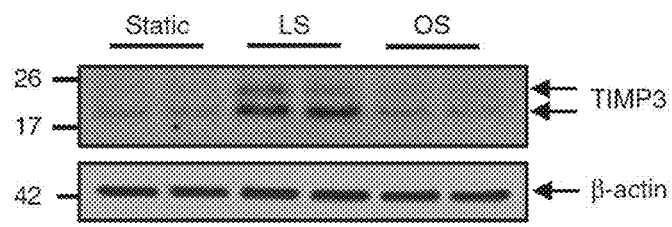
FIG. 3E shows—TIMP3 expression decreased by OS compared with LS for 24 h.
Figure 3F:
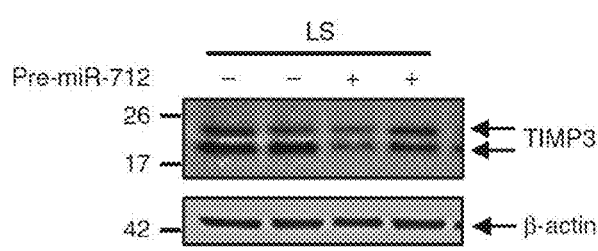
FIG. 3F shows data where treatment with pre-miR-712 (20 nM) downregulated TIMP3 expression under LS condition.
Figure 3G:
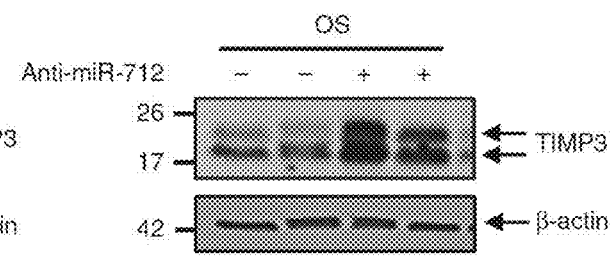
FIG. 3G shows data where anti-miR-712 (400 nM) treatment rescued OS-induced loss of TIMP3. β-actin was used as an internal loading control.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, immunology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Subject" refers any animal, preferably a human patient, livestock, rodent, monkey or domestic pet.

The term "sample" as used herein refers to any biological or chemical mixture for use in the method of the disclosure. The sample can be a biological sample. The biological samples are generally derived from a patient, preferably as a bodily fluid (such as tumor tissue, lymph node, sputum, blood, bone marrow, cerebrospinal fluid, phlegm, saliva, or urine) or cell lysate. The cell lysate can be prepared from a tissue sample (e.g. a tissue sample obtained by biopsy), for example, a tissue sample (e.g. a tissue sample obtained by biopsy), blood, cerebrospinal fluid, phlegm, saliva, urine, or the sample can be cell lysate. In preferred examples, the sample is one or more of blood, blood plasma, serum, cells, a cellular extract, a cellular aspirate, tissues, a tissue sample, or a tissue biopsy.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Inhibition of Mechanosensitive microRNA, miR-712, Atypical microRNA Derived from Pre-Ribosomal RNA, Decreases Endothelial Dysfunction and Atherosclerosis Atherosclerosis typically occurs in arterial regions exposed to disturbed flow (d-flow) by mechanisms involving broad changes in gene expression. While microRNAs (miRNAs) regulate various aspects of cardiovascular biology and disease, their role in atherosclerosis has not previously been directly demonstrated. Vascular endothelial cells respond to blood flow through mechanosensors which transduce the mechanical force associated with flow (known as shear stress) into cell signaling events and changes in gene expression. D-flow and stable flow (s-flow) promotes and inhibits atherogenesis, respectively, in large part by regulating discrete sets of pro-atherogenic and atheroprotective genes. While s-flow upregulates atheroprotective genes such as Klf2, Klf4, and eNOS, d-flow upregulates a number of pro-atherogenic genes including vascular cell adhesion molecule-1 (VCAM-1) and matrix metalloproteinases (MMPs) which mediate pro-angiogenic, pro-inflammatory, proliferative, and pro-apoptotic responses, promoting atherosclerosis.

Using a mouse partial carotid ligation model and endothelial miRNA array mechanosensitive miRNAs were identified. Of those mechanosensitive miRNAs identified, miR-712 was the most shear-sensitive miRNA upregulated by d-flow both in vivo and in vitro. miR-712 is derived from the internal transcribed spacer 2 (ITS2) region of pre-ribosomal RNA (RN45S gene) in a XRN1 exonuclease-dependent, but DGCR8-independent manner, suggesting that it is an atypical miRNA derived from an unexpected source. Studies including gain-of-function (pre-miR-712) and loss-of-function (anti-miR-712) approaches and target-binding assays showed that miR-712 directly downregulated the tissue inhibitor of metalloproteinase 3 (TIMP3) expression. This in turn activated downstream metalloproteinases (MMPs and ADAM family) and stimulated pro-atherogenic responses, endothelial tubule formation and sprouting, in a flow-dependent manner. Further, treatment with anti-miR-712 prevented atherosclerosis in two different models of murine atherosclerosis using ApoE$^{-/-}$ mice: a chronic conventional western-diet or an acute carotid partial ligation model on a high-fat diet. These results indicate that targeting mechanosensitive "athero-miRs" with anti-miR-based approaches is a viable treatment paradigm in atherosclerosis.

Abdominal Aortic Aneurysm Induced by Angiotensin II is Mediated by miR-712 and -205, which Target the Matrix Metalloproteinase Inhibitors, TIMP3 and RECK The Angiotensin II (AngII)-induced abdominal aortic aneurysm (AAA) model is commonly used rodent model that has been well studied because of many features it shares with human AAA. Uncontrolled degradation of the local extracellular matrix by proteases such as MMPs is an initiation step in AAA development. The regulation of protease activity by miRNA in AAA is reported herein. The miRNA-712 and -205 identified in this study in the vasculature are regulated by AngII and play a role in AngII-induced AAA. miR-712 was identified from a miRNA array and its human homolog miR-205 was validated by endothelial-enriched RNAs obtained from C57BL6 mice infused with AngII. Although it is not intended that embodiments of the disclosure be limited by any particular mechanism, it is believed that miR-712 and miR-205 regulate matrix metalloproteases (MMPs) activity through directly targeting two inhibitors of MMPs: tissue inhibitor of metalloproteinase 3 (TIMP3) and reversion inducing cysteine-rich protein with kazal motifs (RECK). Silencing of miR-712 and miR-205 significantly decreased MMP activity in the AngII-infused abdominal aorta wall, prevented dilatation of aorta and significantly reduced AAA incidence. AngII-sensitive miR-NAs, miR-712 and miR-205, regulate MMP activity through TIMP3 and RECK and play a role in the pathogenesis of AAA indicating that targeting these miRNAs using their inhibitors is a therapeutic strategy to prevent the development of AAA and related diseases and conditions.

In Abdominal aortic aneurysm (AAA), a permanent dilation of the abdominal aorta occurs due to a loss of the structural integrity of the vascular wall. AAA is more common disease in subjects above the age of 60 or 65. The most significant cause of mortality from AAA is acute rupture. The progressive weakening and dilation of the aorta observed in AAA is due to the degradation and remodeling of the extracellular matrix (ECM) of the aortic wall. Surgical and mechanical interventions are the only known effective treatments to prevent AAA rupture.

AngII stimulates miR-712 and its human homolog, miR-205 expression in the suprarenal artery, which in turn inhibits TIMP3 and RECK. Downregulation of these MMP endogenous inhibitors creates a permissive environment for unregulated MMP activity in the abdominal aorta, therefore allowing the ECM remodeling leading to AAA. miR-712 is AngII-sensitive miRNA as determined through miRNA array, in situ hybridization and qPCR validation in vitro and in vivo. miR-205 was identified as a human homolog of the murine miR-712. miR-712 and miR-205 regulates metalloproteinase activity by targeting two endogenous inhibitors of MMPs and ADAMs; TIMP3 and RECK. Anti-miR-712 and anti-miR-205 treatment in vivo can effectively silence miR-712 and miR-205 expression in arterial vessel wall cells and blood, restoring TIMP3 levels and inhibiting AAA development.

AAA are characterized by common molecular processes that underlie inflammation and ECM degradation. These changes are associated with an inflammatory infiltrate and excessive production of MMPs, which are assumed to organize the widespread matrix destruction. MMP degrade the ECM proteins, whereas their inhibitors, TIMPs keep their activity in check.

A mouse model to study the pathogenesis of AAA is AngII infusion model using osmotic mini-pump. In humans, there is associative evidence supporting an increase in cardiovascular events with increases in the activity of renin, the rate-limiting step in AngII generation and has been shown to exert direct effects on vascular remodeling and function. The role of AngII in the atherogenic process has been inferred from the survival and ventricular enlargement trial that demonstrated that administration of angiotensin II-converting enzyme (ACE) inhibitors was associated with a decrease in cardiovascular morbidity and mortality. A number of animal experiments reported the relationship between AngII and aneurysm development and the preventive effect of ACE inhibitors and AngII receptor blocker (ARBs). Emerging evidence suggests that the AngII-induced AAA mouse model is a widely used approach to address the pathophysiological mechanism of this disease and rennin-angiotensin system may act as a molecular and therapeutic target for treating AAA.

Mechanisms of MMPs silencing include interaction with the specific TIMPs and other endogenous inhibitors, such as α2-macroglobulin, RECK and tissue-factor pathway-inhibitor 2 (TFPI2). TIMP3 and RECK were identified as target genes of miR-712 and miR-205. TIMPs inhibit a broader spectrum of metalloproteinases, however, not with the same efficacy. Because of this broad inhibitory spectrum, TIMP-3 ablation in mice causes lung emphysema-like alveolar damage whereas TIMP-1-null mice and TIMP-2-null mice do not exhibit obvious abnormalities and loss of TIMP3 promote AAA formation.

RECK was identified as another target gene of miR-712 and miR-205. RECK is a membrane bound protein which, in the mouse, has been found to be important in suppressing MMPs and angiogenesis in the metastatic cascade. miR-712 is a murine-specific miRNA. miR-205 shares the same "seed sequence" with miR-712 which are targets of TIMP3 and RECK.

Nucleobase Polymer Therapeutics

The term "nucleobase polymer" refers to a polymer comprising nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleic acid may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding.

In certain embodiments, the disclosure relates to composition comprising an isolated antisense nucleobase polymers, interference nucleobase polymers and RNA-blocking oligonucleotides.

In certain embodiments, the nucleobase polymers are 8 to 25 base oligomers that mimic DNA or RNA. Many nucleobase polymers differ from native RNA or DNA in the chemical structure that links the four common bases. For example, a RNA may be modified to contain phosphorothioates instead of phosphodiester linkages. Nucleobase polymers that contain phosphorothioates may hybridize to RNA and promote RNase H mediated degradation.

In certain embodiments, nucleobase polymers are contemplated to comprise peptide nucleic acids (PNAs). One example of a peptide nucleic acid is one that has 2-aminoethyl glycine linkages or similar analogs in place of the regular phosphodiester backbone. Other examples include d-lysPNA, argPNA, alternating units of 2-aminocyclopentanoic acid and pyrrolidine-2-carboxylic acid (pyrPNA). See Nielson, Chem & Biodiversity, 2010, 7:786.

In certain embodiments, nucleobase polymers are contemplated to comprise non-natural nucleobases such as, but not limited to, pseudoisocytosine as a substitute for cytosine, diaminopurine as a substitute for adenine, bicyclic thymine analogue (7C1-bT), thiouracil, or combinations thereof.

In certain embodiments, nucleobase polymers are contemplated to comprise phosphorodiamidate morpholino oligomers (PMO). In certain embodiments, the nucleobase polymer comprises monomers of (2-(hydroxymethyl)morpholino)(piperazin-1-yl)phosphinate. In certain embodiments, the disclosure contemplates chemical conjugation of PMO to arginine-rich or cell penetrating peptides (CPP) such as (R-Ahx-R)$_4$ (with Ahx standing for 6-aminohexanoyl), RXRRBRRXR ILFQY RXRBRXRB (SEQ ID NO: 6), RXRRBRRXR YQFLI RXRBRXRB (SEQ ID NO: 7), RXRBRRX-ILFRY-RXRBRXRB (SEQ ID NO: 8), wherein X is 6-aminohexanoyl and B is β-alanine spacers. CPPs may be conjugated to the 3' end of the PMO or to the 5' end or both. See Warren & Bavari, Antiviral Research, 2012, 94(1):80-88 and Betts et al., Molecular Therapy Nucleic Acids, 2012, 1: e38.

In certain embodiments, the disclosure relates to composition comprising an isolated antisense nucleobase polymer that binds RNA of SEQ ID NO: 1 or SEQ ID NO: 11. In certain embodiments, the nucleobase polymer is a nucleic acid or nucleic acid mimetic that hybridizes to RNA of SEQ ID NO: 1 or SEQ ID NO: 11.

In certain embodiments, the antisense nucleobase polymer base comprises more than 10, 15, 20, 30, 40, 50, 60, or 70 nucleobases that base pair—hydrogen bond—with RNA of SEQ ID NO: 1 or SEQ ID NO: 11, or are the reverse complement of RNA of SEQ ID NO: 1 or SEQ ID NO: 11.

In certain embodiments, the nucleobase polymer base comprises one of the following nucleobase sequences which are the miR663 reverse complement and segments:

(SEQ ID NO: 2)
CCUUCCGGCGUCCCAGGCGGGGCGCCGCGGGACCGCCCUCGUGUCUGUGG

CGGUGGGAUCCCGCGGCCGUGUUUUCCUGGUGGCCCGGCCAUG;

(SEQ ID NO: 3)
CCUUCCGGCGUCCCAGGCGGGGCGCCGCGGGACCGCCCUCGUGUCUGUGG

C;

(SEQ ID NO: 4)
GGUGGGAUCCCGCGGCCGUGUUUUCCUGGUGGCCCGGCCAUG;

(SEQ ID NO: 5)
ACCGCCCUCGUGUCUGUGGCGGUGGGAUCCCGCGGC;

In certain embodiments, the nucleobase polymer base comprises one of the following nucleobase sequences which are segments the miR205 reverse complement (SEQ ID NO: 12)
CCGGTGGUUTGUUGGU;

(SEQ ID NO: 13)
TCCUCTGUUUTCTGGTTGGGTUTGUGU (SEQ ID NO: 14)
CUGUCTCCGGTGGUUTGUUGGU;
and (SEQ ID NO: 15)
CUGCTCCUTGCCTCCTGUUCTTCUCTCCUCTGUUUTCTGGTTGGG;

In certain embodiments, the disclosure relates to compounds, compositions, and methods useful for modulating of miR-205 and/or miR-663 using nucleobase polymers. In particular, the instant disclosure features small nucleic acid molecules, such as short interfering short interfering RNA (siRNA), double-stranded RNA (dsRNA), micro-RNA (miRNA), and short hairpin RNA (shRNA) molecules and methods used to modulate the of miR-663.

RNA interference refers to the process of sequence specific post-transcriptional gene silencing in animals mediated by short interfering nucleobase polymers sometimes referred to as post-transcriptional gene silencing or RNA silencing. The presence of long dsRNAs in cells is thought to stimulate the activity of a ribonuclease III enzyme referred to as Dicer. Dicer is thought to be involved in the processing of the dsRNA into short pieces of dsRNA known as short interfering RNAs (siRNAs). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control. The RNAi response is thought to feature an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex. In addition, RNA interference is thought to involve small RNA (e.g., micro-RNA or miRNA) mediated gene silencing, presumably though cellular mechanisms that regulate chromatin structure and thereby prevent transcription of target gene sequences. As such, siNA molecules can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Elbashir et al., 2001, Nature, 411, 494, describe RNAi induced by introduction of duplexes of synthetic 21-nucleotide RNAs in cultured mammalian cells including human embryonic kidney and HeLa cells. Work in Drosophila embryonic lysates has revealed certain preferences for siRNA length, structure, chemical composition, and sequence that mediate efficient RNAi activity. These studies have shown that 21 nucleotide siRNA duplexes are typical when using two 2-nucleotide 3'-terminal nucleotide overhangs. Substitution of 3'-terminal siRNA nucleotides with deoxy nucleotides was shown to be tolerated. Other studies have indicated that a 5'-phosphate on the target-complementary strand of an siRNA duplex is beneficial for siRNA activity and that ATP is utilized to maintain the 5'-phosphate moiety on the siRNA. siRNA molecules lacking a 5'-phosphate are active when introduced exogenously.

A nucleobase polymer can be synthetic or recombinantly produced nucleic acid unmodified or chemically-modified compared to naturally occurring nucleic acids. A nucleic acid can be chemically synthesized, expressed from a vector or enzymatically synthesized. Various chemically-modified synthetic short interfering nucleic acid (siNA) molecules are capable of modulating miR-205 and/or miR-663 activity in cells by RNA interference (RNAi).

In one embodiment, the disclosure relates to a double-stranded short interfering nucleobase polymers that down-regulates miR-205 and/or miR-663 or expression of miR-205 and/or miR-663, wherein said comprising about 15 to about 35 base pairs.

In certain embodiments, the nucleobase polymer or interference nucleic acid is in a hairpin.

In some embodiments, the disclosure relates to methods of treating a subject diagnosed with a vascular condition by administering a pharmaceutical composition with a nucleobase polymer or nucleic acid that is a single strand.

In certain embodiments, this disclosure relates to particles comprising a hydrophilic or lipid membrane and ionizable or cationic core comprising the nucleobase polymer. Siegwart et al. report the synthesis of coreshell nanoparticles by the reaction of epoxide-containing block copolymers with polyethylene glycol monomers and amines. See PNSA, 2011, 108(32):12996-3001.

In certain embodiments, contemplated particles comprise block copolymers of poly(d,l-lactide) (PLA) or poly(d,l-lactide-co-glycolide) (PLGA) and poly(ethylene glycol) (PEG), in which nucleobase polymers were physically entrapped without chemical modification.

In certain embodiments, contemplated particles comprise a hydrophobic biodegradable polymeric core that allows for the encapsulation and controlled release of nucleobase polymers, a hydrophilic shell that protects the nucleobase polymers, and optionally a targeting ligand that mediated molecular interactions between particle and target endothelial cells.

In certain embodiments, contemplated particles comprise a linear polymer in which positively or negatively charged groups alternate with polysaccharides (e.g., cyclodextrin). Upon mixing with nucleobase polymers, the positively or negatively charged polymer respectively associates with the negatively or positively charged backbone of nucleobase polymers, nucleic acids, or RNAs. Several polymer/complexes self-assemble into a nanoparticle that fully protects the molecules from degradation in serum. Formation of inclusion complexes between adamantane (AD) and O-cyclodextrin allows noncovalent incorporation of stabilizing (via PEG-AD conjugates) and/or targeting (via ligand-PEG-AD conjugates) components to a polymer-nucleic acid nanoparticles (polyplex). See Suzie & Davis, Bioconjugate Chemistry, 2002, 13(3):630-639. Directly conjugating the nucleobase polymer to a cyclodextrin-based polymer is also contemplated. See Heidel & Schluep, "Cyclodextrin-Containing Polymers: Versatile Platforms of Drug Delivery Materials," J Drug Delivery, 2012, Article ID 262731, 17 pages.

In certain embodiments, the disclosure relates to a nucleobase polymers disclosed herein optionally conjugated to a detectable marker or label such as, but not limited to, a fluorescent dye, radio isotope, stable isotopes with lower natural abundance, positron-emitting radionuclide (tracer), antibody epitope, biotin, ligand, steroid, quantum dot. Useful physical properties include a characteristic electromagnetic spectral property such as emission or absorbance, magnetism, electron spin resonance, electrical capacitance, dielectric constant or electrical conductivity. The marker may be ferromagnetic, paramagnetic, diamagnetic, luminescent, electrochemiluminescent, fluorescent, phosphorescent, chromatic or have a distinctive mass. Fluorescent moieties which are useful as markers include dansyl fluorophores, coumarins and coumarin derivatives, fluorescent acridinium moieties and benzopyrene based fluorophores and quantum dots. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity, positron emission tomography, and nuclear magnetic resonances and use of a mass spectrometer to detect presence of a marker with a specific molecular mass.

Synthesis of Nucleobases Polymers

Small nucleobase polymers and nucleic acid motifs ("small" refers to nucleic acid motifs no more than 100 nucleotides in length, preferably no more than 80 nucleotides in length, and most preferably no more than 50 nucleotides in length; e.g., individual oligonucleotide sequences or sequences synthesized in tandem) are preferably used for exogenous delivery. Exemplary molecules of the instant disclosure are chemically synthesized, and others can similarly be synthesized.

One synthesizes oligonucleotides (e.g., certain modified oligonucleotides or portions of oligonucleotides) using protocols known in the art as, for example, described in U.S. Pat. No. 6,001,311. The synthesis of oligonucleotides makes use of common nucleic acid protecting and coupling groups, such as dimethoxytrityl at the 5'-end and phosphoramidites at the 3'-end. In a non-limiting example, small scale syntheses are conducted on a 394 Applied Biosystems, Inc. synthesizer using a 0.2 micro mol scale protocol with a 2.5 min coupling step for 2'-O-methylated nucleotides and a 45 second coupling step for 2'-deoxy nucleotides or 2'-deoxy-2'-fluoro nucleotides. Alternatively, syntheses at the 0.2 micro mol scale can be performed on a 96-well plate synthesizer, such as the instrument produced by Protogene (Palo Alto, Calif.) with minimal modification to the cycle. A 33-fold excess of 2'-O-methyl phosphoramidite and a 105-fold excess of S-ethyl tetrazole can be used in each coupling cycle of 2'-O-methyl residues relative to polymer-bound 5'-hydroxyl. A 22-fold excess of deoxy phosphoramidite and a 70-fold excess of S-ethyl tetrazole mop can be used in each coupling cycle of deoxy residues relative to polymer-bound 5'-hydroxyl. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM 12, 49 mM pyridine, 9% water in THF (PerSeptive Biosystems, Inc.). S-Ethyltetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

Deprotection of the DNA-based oligonucleotides is performed as follows: the polymer-bound trityl-on oligonucleotide is transferred to a 4 mL glass screw top vial and suspended in a solution of 40% aqueous methylamine (1 mL) at 65 degrees for 10 minutes. After cooling to −20 degrees, the supernatant is removed from the polymer support. The support is washed three times with 1.0 mL of EtOH:MeCN:H2O/3:1:1, vortexed and the supernatant is then added to the first supernatant. The combined supernatants, containing the oligonucleotide, are dried.

Alternatively, the nucleic acid molecules can be synthesized separately and joined together post-synthetically, for example, by ligation or by hybridization following synthesis and/or deprotection.

Nucleic acids can also be assembled from two distinct nucleic acid strands or fragments wherein one fragment includes the sense region and the second fragment includes the antisense region of the RNA molecule.

The nucleic acid molecules can be modified extensively to enhance stability by modification with nuclease resistant groups, for example, 2'-amino, 2'-C-allyl, 2'-fluoro, 2'-O-methyl, 2'-H). Constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See e.g., U.S. Pat. Nos. 5,652,094, 5,334,711, and 6,300,074. All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

In one embodiment, nucleic acid molecules include one or more (e.g., about 1, 2, 3, 4, 5, 6, 7, 8, 9, 10, or more) G-clamp nucleotides. A G-clamp is a tricyclic aminoethyl-phenoxazine 2'-deoxycytidine or analogue. See Lin &. Matteucci, J Am Chem Soc, 1998, 120, 8531-8532; Flanagan, et al., Proc Nat Acad Sci USA, 1999, 96, 3513-3518; and Maier, et al., Biochemistry, 2002, 41, 1323-1327. A single G-clamp analog substitution within an oligonucleotide can result in substantially enhanced helical thermal stability and mismatch discrimination when hybridized to complementary oligonucleotides. The inclusion of such nucleotides in nucleic acid molecules results in both enhanced affinity and specificity to nucleic acid targets, complementary sequences, or template strands.

In another embodiment, nucleic acid molecules include one or more (e.g., about 1, 2, 3, 4, 5, 6, 7, 8, 9, 10, or more) LNA "locked nucleic acid" nucleotides such as a 2',4'-C methylene bicyclo nucleotide (see for example U.S. Pat. Nos. 6,639,059, 6,670,461, 7,053,207).

In another embodiment, the disclosure features conjugates and/or complexes of nucleobase polymers. Such conjugates and/or complexes can be used to facilitate delivery of polymers into a biological system, such as a cell. Contemplated conjugates include those with cell penetrating peptide. The conjugates and complexes provided may impart therapeutic activity by transferring therapeutic compounds across cellular membranes, altering the pharmacokinetics, and/or modulating the localization of nucleic acid molecules. In general, the transporters described are designed to be used either individually or as part of a multi-component system, with or without degradable linkers. These compounds improve delivery and/or localization of nucleic acid molecules into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

In yet another embodiment, nucleobase polymers having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

In another aspect a nucleobase polymers comprises one or more 5' and/or a 3'-cap structure, for example on only the sense strand, the antisense strand, or both strands.

A "cap structure" refers to chemical modifications, which have been incorporated at either terminus of the oligonucleotide. See, for example, Adamic et al., U.S. Pat. No. 5,998, 203. These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925).

In one embodiment, the disclosure features modified nucleobase polymer, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkyl silyl, substitutions.

Pharmaceutical Compositions

The following protocols can be utilized for the delivery of nucleobase polymers. A nucleobase polymer can be adapted for use to prevent or treat a vascular disease or condition that is related to or will respond to the levels of miR-205 and/or miR-663 in the blood, a cell, or tissue, alone or in combination with other therapies. For example, a nucleobase polymer can be contained in a delivery vehicle, including liposomes, for administration to a subject, carriers and diluents and their salts, and/or can be present in pharmaceutically acceptable formulations. U.S. Pat. Nos. 6,395,713 and 5,616,490 further describe general methods for delivery of nucleic acid molecules. Nucleobase polymers can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example U.S. Pat. Nos. 7,141,540 and 7,060,498), poly(lactic-co-glycolic)acid (PLGA) and PLCA microspheres (see for example U.S. Pat. No. 6,447,796), biodegradable nanocapsules, and bioadhesive microspheres, or by proteinaceous vectors (U.S. Pat. No. 7,067,632). In another embodiment, the nucleobase polymers can also be formulated or complexed with polyethyleneimine and derivatives thereof, such as polyethylene-imine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In one embodiment, a nucleobase polymers is complexed with membrane disruptive agents such as those described in U.S. Pat. No. 6,835,393. In another embodiment, the membrane disruptive agent or agents and nucleobase polymers are also complexed with a cationic lipid or helper lipid molecule, such as those lipids described in U.S. Pat. No. 6,235,310.

Embodiments of the disclosure feature a pharmaceutical composition comprising one or more nucleobase polymers in an acceptable carrier, such as a stabilizer, buffer, and the like. The nucleobase polymers or oligonucleotides can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions can also be formulated and used as tablets, capsules or elixirs for oral administration, suppositories for rectal administration, sterile solutions, suspensions for administration by injection, and the other compositions known in the art.

Embodiments of the disclosure also feature the use of the composition comprising surface-modified liposomes containing poly (ethylene glycol) lipids (PEG-modified, or long-circulating liposomes or stealth liposomes). These formulations offer a method for increasing the circulation and accumulation of in target tissues. The long-circulating liposomes enhance the pharmacokinetics and pharmacodynamics of DNA and RNA. See U.S. Pat. Nos. 5,820,873 and 5,753,613. Long-circulating liposomes are also likely to protect from nuclease degradation.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Methods of Use

In certain embodiments, the disclosure relates to methods of treating or preventing a vascular disease or condition comprising administering an effective amount of a pharmaceutical composition disclosed herein to a subject in need thereof.

In certain embodiments, the disclosure relates to methods of treating or preventing a vascular disease condition comprising administering an effective amount of a pharmaceutical composition comprising an nucleobase polymer or RNAi method disclosed herein or a particle comprising RNAi composition disclosed herein.

In certain embodiments, the disclosure relates to methods for inhibiting or preventing atherosclerosis, aortic aneurysm, rheumatoid arthritis and cancer in human patients by treating them with using an effective amount of a compound that inhibits miR-205/miR-712/miR-663 family, which in turn increases or preserves expression of tissue inhibitor of metalloproteinease-3 (TIMP3) and reversion-inducing cysteine-rich protein with Kazal motifs (RECK), wherein said compound is selected from the group consisting of microRNA inhibitors of miR-712/miR-205/miR-663 family by using nucleic acid sequences that complement the whole or a part of the miRNA sequence such as the seeding sequence. The nucleic acid inhibitors can be synthesized by using locked nucleic acid (LNA)-based designs.

In certain embodiments, the disclosure relates to methods comprising administering an effective amount of a microRNA-712/miR-205/miR-663 antagonist to the diseased tissues and cell types.

In certain embodiments, the subject is a human that is at risk of, exhibiting symptoms of, or diagnosed with atherosclerosis, peripheral vascular disease, coronary heart disease, heart failure, right ventricular hypertrophy, cardiac dysrhythmia, endocarditis, inflammatory cardiomegaly, myocarditis, vascular heart disease, stroke, cerebrovascular disease, or peripheral arterial disease.

In certain embodiments, the subject has type I or type II diabetes, impaired glucose tolerance, elevated serum C-reactive protein concentration, vitamin B6 deficiency, dietary iodine deficiency, hypothyroidism, hyperlipidemia, hypertension, or is older than 50 years old, or smokes cigarettes daily.

In certain embodiments, the pharmaceutical composition is administered in combination with a statin, atorvastatin, cerivastatin, fluvastatin, lovastatin, mevastatin, pitavastatin, pravastatin, rosuvastatin, simvastatin, ezetimibe, amlodipine, niacin, aspirin, omega-3 fatty acid, or combinations thereof.

In certain embodiments, the therapy is delivered by intravenous or intramyocardial injection. In certain embodiments, the intramyocardial injection is delivered during surgery. In certain embodiments, the intramyocardial injection is delivered percutaneously using one or more catheters. In certain embodiments, the intramyocardial injection is directly into the epicardium. In certain embodiments, the therapy is delivered by intrapericardial injection. In certain embodiments, the method of delivery is combined with one or more vasodilatory agents.

In certain embodiments, one or more of the above therapies is administered in combination with one or more other therapies for cardiovascular disease.

In certain embodiments, the disclosure relates to medical devices, such as stents, e.g., mesh tube comprising compositions disclosed herein, e.g., recombinant TIMP3, antisense nucleobase polymers, blocking oligonucleotide, gene therapy vectors, and RNA interference therapeutic compositions.

In certain embodiments, the disclosure relates to using compositions disclosed herein coated or conjugated or integrated into vascular or non-vascular medical devices, stents, pace makers, guide wires, delivery balloons, catheters, bioresorbable vascular scaffolds, embolic protection devices and others. Molecular compositions can be linked to polymers on the surface of the devices or integrated to release with biodegradable polymers.

In certain embodiments, the disclosure relates to a gene therapy using a vector that expresses human TIMP3 in human cells. In certain embodiments, the disclosure relates to methods for inhibiting or preventing atherosclerosis, aortic aneurysm, rheumatoid arthritis and cancer in human patients by treating them with using an effective amount a vector that expresses TIMP3 in human cells. In some embodiments, the disclosure relates to methods of treating a subject diagnosed with a vascular condition by administering an effective amount a vector that expresses TIMP3 in human cells.

In certain embodiments, the disclosure relates to gene therapy. The gene therapy typically comprises a recombinant viral vector. In certain embodiments, the viral vector is a recombinant retrovirus. In certain embodiments, the retroviral vector is a recombinant lentivirus. In certain embodiments, the viral vector is a recombinant adenovirus. In certain embodiments, the viral vector is a recombinant adeno-associated virus (rAAV) of any rAAV serotype.

In certain embodiments, the gene therapy comprises a non-viral vector. In certain embodiments, the non-viral vector is plasmid DNA. In certain embodiments, the non-viral vector is a polymer-DNA complex. In certain embodiments, the non-viral vector is a liposome-DNA complex.

Recombinant viral vectors include, but are not limited to, recombinant adeno-associated virus (rAAV), recombinant retrovirus, recombinant adenovirus, recombinant poxvirus, and recombinant herpes simplex virus (HSV). The choice of recombinant viral vector used depends on the type of genetic material (e.g. RNA or DNA, single-stranded or double-stranded) to be transferred to the target cell. Several types of retrovirus are available including, but not limited to, lentivirus and gamma-retrovirus (e.g. murine leukemia virus), with lentivirus being the typical choice. A retrovirus may be used to transfer RNA, which is subsequently incorporated randomly into the target cell's genome by the enzymes reverse transcriptase and integrase. Multiple serotypes of rAAV (e.g. AAV1, AAV2, and other AAV serotypes) may be used. rAAV may be used to transfer single-stranded DNA. Recombinant adenovirus does not incorporate into a target cell's genome, but rather expresses free DNA in the nucleus and may be considered transient. Recombinant adenovirus may be used to transfer double-stranded DNA. Poxvirus is used to transfer double-stranded DNA. HSV is typically used to target neurons as it is capable of latently infecting those cells. HSV may be used to transfer double-stranded DNA. Of the viral vector methods of gene therapy, rAAV-mediated gene delivery is the typical choice. rAAV is considered non-immunogenic, i.e. an individual will not typically mount an immune response to clear it, and it is capable of infecting non-dividing, quiescent cells.

In certain embodiments, the disclosure relates to 10, 15 or 20 or more nucleotide segments of microRNA-712/miR-205/miR-663 that are expressed by a vector to form small hairpin RNA. In certain embodiments, the disclosure relates to vectors that express a small hairpin RNA wherein the double stranded portion contains a 10, 15 or 20 or more nucleotide segment of microRNA-712/miR-205/miR-663. RNA molecules may be used to interfere with gene expression. Small hairpin RNA (shRNA), also known as short hairpin RNA, may be introduced into a target cell and may be constitutively expressed by the H1 or U6 promoters. The shRNA is capable of inhibiting target gene expression by RNA interference. shRNA is cleaved, forming small interfering RNA (siRNA). siRNAs are double-stranded. The RNA-induced silencing complex binds to the siRNA, and the siRNA in turn binds to a target mRNA sequence which is then cleaved. This may be used to disrupt mRNA translation. Antisense RNA may also be used to modulate mRNA translation. Antisense RNA is single-stranded RNA that binds to complementary mRNA thereby obstructing its ability to translate.

Gene therapy is currently a well-characterized, established methodology with both viral and non-viral delivery well-known in the art. For example, clinical trial were conducted to restore the levels of the sarcoplasmic reticulum $Ca^{2+}$-ATPase enzyme in patients with advanced heart failure by gene transfer with the use of a viral vector (AAV1) to deliver the SERCA2a gene, demonstrating safety and feasibility. See Rapti et al., Can J Cardiol., 2011; 27(3):265-83. See also Herzog et al., "Two decades of Clinical gene therapy—success is finally mounting" Discov Med. 2010; 9(45):105-11. Other examples of diseases in which clinical trials are being conducted by use of gene therapies include α1 antitrypsin, Batten's disease, Canavan's disease, Cystic fibrosis, Haemophilia B, Leber's congenital amaurosis, Pompe's disease, Muscular dystrophy, Parkinson's disease, Age-related macular degeneration, and Rheumatoid arthritis. See Mingozzi & High, Nat Rev Genet. 2011, 12(5):341-55.

One ordinarily skilled in the art will be capable of creating and administering a recombinant viral vector for the purpose of gene therapy. A recombinant viral vector may be created by a process comprising isolating the transgene of interest, incorporating it into a recombinant viral expression vector (the construct), and administering the construct to the target in order to incorporate the transgene. Numerous recombinant viral expression vectors are commercially available for these purposes. The exact protocol for generating a recombinant viral vector may vary depending on the choice of the viral vector. Example protocols for generating rAAV, the typical choice of viral vector, as well as recombinant retrovirus are disclosed in Heilbronn R, Weger S., Viral vectors for gene transfer: current status of gene therapeutics. Handb Exp Pharmacol. 2010, (197):143-70.

In certain embodiments, the disclosure relates to the treatment or prevention of an inflammatory disorder comprising compositions disclosed herein in an effective amount to a subject in need thereof. Contemplated inflammatory disorders include, but not limited to, acne vulgaris, asthma, celiac disease, chronic prostatitis, glomerulonephritis, hypersensitivities, inflammatory bowel disease, pelvic inflammatory disease, reperfusion injury, rheumatoid arthritis, sarcoidosis, transplant rejection, vasculitis, interstitial cystitis, atherosclerosis, allergies, hay fever, myopathies, leukocyte defects, a vitamin A deficiency and autoimmune diseases.

Examples miR-712 was the Most Consistently and Robustly Upregulated miRNA Both In Vivo and In Vitro Vascular endothelial cells respond to blood flow through mechanosensors which transduce the mechanical force associated with flow (known as shear stress) into cell signaling events and changes in gene expression. D-flow and stable flow (s-flow) promotes and inhibits atherogenesis, respectively, in large part by regulating discrete sets of pro-atherogenic and atheroprotective genes. While s-flow upregulates atheroprotective genes such as Klf2, Klf4, and eNOS, d-flow upregulates a number of pro-atherogenic genes including vascular cell adhesion molecule-1 (VCAM-1) and matrix metalloproteinases (MMPs) which mediate pro-angiogenic, pro-inflammatory, proliferative, and pro-apoptotic responses, promoting atherosclerosis.

A mouse model of flow-induced atherosclerosis by partially ligating the left carotid artery (LCA) of the ApoE$^{-/-}$ mouse is reported in Nam et al., American journal of physiology Heart and circulatory physiology, 2009, 297(4): H1535-1543. This model directly demonstrates the causal relationship between d-flow and atherosclerosis as the LCA rapidly develops robust atherosclerosis within two weeks following partial ligation that causes d-flow with characteristic low and oscillatory shear stress (OS), while the contralateral, undisturbed right common carotid artery (RCA) remains healthy. In addition, a method of isolating intimal RNA from mouse carotid artery following ligation has been developed. This method allows easy and rapid endothelial-enriched RNA isolation that is virtually free of contamination from the vascular smooth muscle cells and leukocytes. Using this mouse model and the RNA isolation method, more than 500 mechanosensitive genes were discovered, including ones such as lmo4, klk10, and dhh, and confirming well-known ones, such as VCAM-1, klf2 and eNOS5. However, the effect of d-flow on endothelial miRNAs, especially in vivo, has not been clear. To identify mechanosensitive miRNAs in arterial endothelium in vivo, endothelial miRNA array analyses was carried out using the mouse partial carotid ligation model and integrated these two genome-wide data-sets using a systems biology approach to help us identify relevant miRNA-target gene connection.

The in vivo microarray data showed that 45 (27 up- and 18 downregulated) miRNAs were altered by more than 50% in the LCA endothelium compared to the RCA at 48 hours post-ligation. Quantitative PCR (qPCR) using additional independent RNA samples was used to validate the miRNA array data for the top 10 most mechanosensitive miRNAs (5 up-, 5 down-regulated miRNAs at 48 hours post-ligation): upregulated (miR-330*, 712, 699, 223 and 770-5p) and down-regulated (miR-195, 30c, 29b, 26b and let-7d) miR-NAs. To determine whether these mechanosensitive miR-NAs that were identified in vivo responded specifically to shear stress, expression of these miRNAs was tested in vitro using immortalized mouse aortic endothelial cells (iMAECs) that were subjected to laminar (LS) or oscillatory stress (OS), mimicking s-flow and d-flow in vivo, respectively. These results showed that miR-712 was the most consistently and robustly upregulated miRNA both in vivo and under flow conditions in vitro, leading us to further characterize its expression and function.

In Situ Hybridization with a miR-712 Probe Showed Significantly Increased Expression of miR-712 in the LCA Endothelium A time-course study showed that miR-712 was upregulated significantly in the d-flow region (LCA) compared to s-flow region (RCA) at 48 h post-ligation in mouse carotids. Using the miScript qPCR assay, pre-miR-712 expression significantly increased at 48 h post-ligation while expression of mature-miR-712 increased significantly in LCA at 24 and 48 h post-partial ligation, which was subsequently validated by sequencing the PCR amplicons. This suggests that initial processing of pre-miR-712 into the mature form precedes (24h) the active synthesis of pre-miR-712 (48h) in mouse artery in vivo. Exposure of mouse aortic endothelial cells (iMAECs) to oscillatory shear stress for 24 h in vitro also dramatically increased expression of mature and precursor forms of miR-712 compared to laminar shear, confirming the flow-sensitivity of miR-712 both in vivo and in vitro. Studies using in situ hybridization with a miR-712 probe (Exiqon) showed significantly increased expression of miR-712 in the LCA endothelium, but not in control RCA, further validating the microarray and qPCR results. To determine whether increased expression of miR-712 in LCA was not simply due to an acute change in mechanical environment created by the partial ligation surgery, we tested expression of miR-712 in mouse aortic arch, where the atherosclerosis-prone lesser curvature (LC) and athero-protected greater curvature (GC) are naturally and chronically exposed to d-flow and s-flow, respectively. Expression of miR-712 was significantly higher in the flow-disturbed LC compared to GC. These findings suggest that miR-712 is indeed a flow-sensitive miRNA, which is significantly upregulated in endothelial cells exposed to d-flow in the aortic arch naturally or in LCA upon partial carotid ligation, or in vitro.

Ribosomal RNAs a Source of miRNAs and siRNA Treatment Increased the Expression of miR-712

The genomic locus and biogenesis pathway of miR-712 were not known. A nucleotide sequence search revealed that the pre-miR-712 sequence matched to the internal transcribed spacer region 2 (ITS2) region of the murine pre-ribosomal RNA, RN45s gene, which is still not completely annotated. The Rn45S encodes for 45S, which contains sequences for 18S, 5.8S and 28S rRNAs along with two intervening spacers, ITS1 and ITS2. Since ribosomal RNAs have never been reported to be a source of miRNAs, whether miR-712 biogenesis was regulated by the canonical pathway using the DGCR8/DROSHA and DICER microRNA processors or by non-canonical pathways in a flow-dependent manner was examined. Expression of DICER1 and DGCR8 was not regulated by flow in endothelial cells in vitro (iMAEC) and in vivo (mouse carotids and aortic arch). Since, XRN1 is an exonuclease that is known to degrade the ITS2 region during the processing of RN45s, whether XRN1 is shear-dependent and regulates biogenesis of miR-712 was tested. It was found that XRN1 expression was downregulated by d-flow in the mouse carotid and aortic arch and in endothelial cells in vitro. Further, knockdown of XRN1 by siRNA treatment increased the expression of miR-712, suggesting that reduction of XRN1 under d-flow conditions led to accumulation of miR-712. In contrast, knockdown of the canonical miRNA processor DGCR8 did not affect miR-712 expression. These results suggest that miR-712 is a murine-specific, non-canonical miRNA derived from an unexpected source, pre-ribosomal RNA, in a XRN1-dependent, but DGCR8-independent and DICER1-dependent manner.

Murine-miR-712 and Human miR-663 Serve as Pro-Atherogenic miRNAs

To test whether this novel mechanism of miRNA biogenesis from pre-ribosomal RNA exists in humans as well, we examined human RN45S gene for putative miRNAs using a computational predication program, miREval. This search revealed that human-specific miR-663 could be derived from RN45s gene, in addition to its previously annotated genomic locus on chromosome 2 (miRBase). Interestingly, like miR-712, miR-663 was previously identified from a microarray study as one of the most shear-sensitive miRNAs in human endothelial cells and was shown to induce endothelial inflammation, a key atherogenic step, raising the possibility that they share a common biogenesis pathway and roles in endothelial function. Consistent with this hypothesis, we found that XRN1 expression is inhibited by oscillatory shear stress and that siRNA knockdown of XRN1 significantly increased miR-663 expression in human endothelial cells. These results indicate that murine-miR-712 and human miR-663 could be derived from respective RN45s genes by a common mechanism involving XRN1 and serve as pro-atherogenic miRNAs.

miR-712 is Responsible for Metalloproteinase-Dependent Matrix Dysregulation in Endothelium in a TIMP3-Dependent Manner Through in silico analysis using miR-712 predicted target gene list from TargetScan and the mechanosensitive gene list using the same mouse model, TIMP3 was identified as a potential gene target. TIMP3 was selected for further study since the miR-712 interactome analysis suggested its potential role as a key gene hub connected to numerous genes of interest, including matrix metalloproteinases-2/9 (MMP2/9) and a disintegrin and metalloproteinase 10 (ADAM10), a disintegrin and metalloproteinase with thrombospondin type 1 motif, 4 (ADAMTS4) and versican that are known to play a role in the regulation of pathophysiological angiogenesis and atherosclerosis.

To test whether miR-712 directly targets TIMP3 in endothelial cell, a dual luciferase reporter assay was employed in iMAECs transfected with either wild-type or mutated TIMP3 3'-UTR firefly luciferase constructs. Treatment of cells with pre-miR-712 inhibited luciferase activity in a dose-dependent manner, while mutant or control pre-miR had no effect, demonstrating that miR-712 directly binds TIMP3 3'-UTR and inhibits its expression in endothelial cells.

Whether TIMP3 expression was regulated by flow in a miR-712-dependent manner was tested. Exposure of iMAECs to oscillatory shear for 24 h significantly decreased TIMP3 mRNA and protein expression, compared to laminar shear. Pre-miR-712 treatment decreased expression of TIMP3 in laminar shear-exposed cells, while inhibition of miR-712 using locked nucleic acid (LNA)-based anti-miR-712 increased TIMP3 expression in cells exposed to oscillatory shear. These findings demonstrate that miR-712 upregulated by oscillatory shear, is directly responsible for the loss of TIMP3 expression in endothelial cells.

Inhibition of miR-712 by Anti-miR-712 Treatment or Overexpression of TIMP3 can Overcome Endothelial Dysfunction To examine whether d-flow-induced miR-712 was responsible for metalloproteinase-dependent matrix dysregulation in endothelium in a TIMP3-dependent manner, endothelial tubule formation and sprouting was studied as functional markers of extracellular matrix change in vascular pathophysiology. Endothelial tubule formation was stimulated by exposing cells to oscillatory shear compared to laminar shear. This oscillatory shear-induced endothelial tubule formation was inhibited by anti-miR-712 treatment, while pre-miR-712 treatment increased tubule formation in laminar shear stressed cells. Further, the tubule formation induced by pre-miR-712 treatment was completely prevented by TIMP3 overexpression, while siRNA-mediated knockdown of TIMP3 robustly stimulated tubule formation with or without pre-miR-712. Similarly, endothelial sprouting was stimulated by miR-712 overexpression, which was abrogated by TIMP3 overexpression. These results indicate that mechanistically TIMP3 is downstream of miR-712 and inhibition of miR-712 by anti-miR-712 treatment or overexpression of TIMP3 can overcome endothelial dysfunction induced by d-flow in a miR-712/TIMP3 dependent manner.

LNA-Based Anti-miR-712 Regulates TIMP3 Expression In Vivo

Next, to test whether d-flow-induced miR-712 plays a key role in atherosclerosis, mice were treated with LNA-based anti-miR-712. It was found that anti-miRs can be effectively delivered to arterial endothelium in vivo as demonstrated by two independent methods: confocal en face imaging of TexasRed-labeled control LNA-anti-miR and autoradiography of 64Cu-labelled anti-miR-712. Interestingly, both fluorescent-labeled anti-miR and radiolabelled anti-miR preferentially accumulated in the flow-disturbed LCA and aortic arch, which is likely due to increased endothelial mass transfer and permeability to macromolecules in d-flow areas. A dose-curve study showed that anti-miR-712 (5 mg/kg dose, injected via s.c.) effectively inhibited d-flow-induced miR-712 expression in LCA endothelium as compared to the mismatched control, and this dose was used for all subsequent studies. We found that expression of TIMP3 mRNA and protein was reduced in d-flow regions both in the partially ligated LCA and aortic arch LC compared to RCA and GC, respectively, and it was rescued by the anti-miR-712 treatment. This further demonstrates the role of miR-712 in regulation of TIMP3 expression in a flow-dependent manner in vivo. Since TIMP3 is a well-known inhibitor of MMPs and ADAMs, the effect of anti-miR-712 was examined on these metalloproteinase activities in vivo. MMP activity (in situ zymography) and ADAMs activity (versican cleavage by immunohistochemical staining) were increased by d-flow in LCA compared to RCA which were significantly blunted by anti-miR-712 treatment. These in vivo results, taken together with the endothelial tubule formation and sprouting results in vitro, provide strong evidence for a direct hierarchal link between d-flow, miR-712, TIMP3, and its downstream metalloproteinase activity in arterial wall.

Inhibitory Effect of Anti-miR-712 in Two Different Murine Models of Atherosclerosis The role of miR-712 in atherosclerosis was tested in two different models of atherosclerosis using ApoE$^{-/-}$ mice: (1) the partial carotid ligation model fed a high-fat diet that rapidly develops atherosclerosis within 2 weeks 5 and (2) the conventional western diet-fed model that chronically develops atherosclerosis in 3 months 45. In the carotid ligation model, the LCA rapidly developed atherosclerosis within 2 weeks and treatment with anti-miR-712 (5 mg/kg/day, s.c. twice a week for 2 weeks) significantly reduced atherosclerosis lesion development and immune cell infiltration compared to the mismatched-anti-miR-712 or saline controls. Similarly, anti-miR-712 treatment (5 mg/kg/day, s.c. twice a week for 3 months) significantly inhibited atherosclerosis development in the conventional western diet model in whole aortas as well as in the aortic arch. In both models, anti-miR-712 did not affect the serum lipid profile. These findings demonstrate a potent inhibitory effect of anti-miR-712 in two different murine models of atherosclerosis.

These results demonstrate the hierarchal link between d-flow, miR-712, TIMP3, and its downstream metalloproteinase to endothelial dysfunction and atherosclerosis. Although it is not intended that embodiments of this disclosure be limited by any particular mechanism, it is believed that d-flow sensed by mechanosensors in endothelium reduces the expression of XRN1, which increases miR-712 expression derived from the pre-ribosomal RNA. It is believed that increased miR-712 downregulates TIMP3 expression, which in turn activates MMPs and ADAM proteases, leading to arterial wall matrix fragmentation, endothelial dysfunction and atherosclerosis. Targeting these metalloproteinase regulators by anti-miRs may serve as a therapeutic approach to treat atherosclerosis.

LNA-Based Anti-miR Inhibitor Treatment In Vivo.

For in vivo delivery of anti-miR, inhibition of miR-712 in artery, and functional test of miR-712 on atherosclerosis, locked nucleic acid (LNA)-based miRNA inhibitor (anti-miR-712, Exiqon) were subcutaneously (s.c.) administered to mice. To test delivery efficiency of anti-miR into mouse arterial endothelium, C57BL/6 mice (n=3) were subcutaneously administrated with 5 mg/kg dose of Texas-Red-615-labeled anti-miR-control (TEX615/ACGTC-TATACGCCCA) (SEQ ID NO: 9) or saline. After 24 hour post injection, animals were sacrificed by $CO_2$ inhalation and perfusion with saline containing heparin, followed by a second perfusion with 10% formalin. Aortas were carefully excised, dissected free of surrounding fat tissues. The tissue samples from LCA and RCA as well as the aortic arch were then mounted on glass slides using aqueous fluorescence mounting medium (Dako) after counterstaining with 4',6-diamidino-2-phenylindole (DAPI, Sigma). Samples were imaged using a Zeiss LSM 510 META confocal microscope (Carl Zeiss). To study the inhibition of miR-712 in in vivo settings, LNA-based anti-miR-712 (GTACCGCCCGGGT-GAAGGA) (SEQ ID NO: 10) or mismatched control was subcutaneously administered to C57BL/6 mice (n=4) in an increasing dose of 5, 20 and 40 mg/kg on the day before partial ligation surgery and on the day of partial ligation surgery. Animals were sacrificed on the 4 day post ligation and the carotid intimal RNAs were extracted and expression of miR-712 was determined by qPCR. For the functional testing of miR-712 on atherosclerosis, anti-miR-712 or mismatched-control was subcutaneously administered (5 mg/kg) to ApoE-/- mice (n=10) at one day before partial ligation surgery, on the day of partial ligation surgery and every third day thereafter for 2 weeks. Mice were fed HFD for entire duration of the experiment. Aortic trees were dissected out and processed for subsequent plaque analysis and immunohistochemical analysis.

Synthesis of anti-miR712-DOTA.

The conjugation of 5'-modified anti-miR-712 (5'-/5AmMC6/+CGCCCGGGTGAAGA (SEQ ID NO: 16)-3', Exiqon, and DOTA-NHS-ester (1,4,7,10-tetraazacyclododecane-1,4,7,10-tetraacetic acid mono (N-hydroxysuccinimide ester), Macrocyclics) followed a Hnatowich et al., Journal of pharmacology and experimental therapeutics, 1996, 276(1): 326-334, with modifications. 5'-modified anti-miR-712 (0.19 μmol, 1 mg) was suspended in 0.2 M borated buffer (0.3 mL, pH 8.5) and the dimethylsulfoxide solution (20 μL, Aldrich) of DOTA-NHS-ester (3.6 μmol, 2.8 mg) was added. After 5 hours of reaction at room temperature, the mixture of DOTA conjugated anti-miR-712 was purified on Sephadex G-25 filled with double distilled water (GE healthcare, exclusion limit >5 k) to remove excess residual DOTA-NHS-ester. Isolated anti-miR-712-DOTA was then purified by HPLC monitored by absorbance (260 nm), with the following HPLC conditions: column Clarity Oligo-PR (250×10.00 mm, 5 micron, Phenomenex), gradient-solvent B (5-30%, 0-30 min, solvent A-0.1 M triethylammonium acetate (TEAA), solvent B-acetonitrile). Collected fractions were concentrated by centrifugation with an Amicon Ultra-4 centrifugal filter unit (MWCO: 3 k). Double distilled water (4 mL) was added to the filter unit and the mixture was concentrated again by centrifugation. The washing procedure was repeated 6 times to remove triethylammonium acetate salt. The concentrated solution was lyophilized and anti-miR-712-DOTA was stored at -20° C. MS analysis of sample was performed with Thermo Fisher Scientific LTQ Orbitrap (San Jose, Calif.) operated in the centroid mode. The deconvoluted mass from 1413.43 (Z=4) was detected at 5657.7 (Calc MW=5657.6)

Radiolabeling of Anti-miR-712-DOTA $^{64}CuCl_2$ was purchased from MIR Radiological Sciences (Washington University Medical School, St. Louis, Mo.) under a protocol controlled by the University of California, Davis. $^{64}CuCl_2$ (3-5 mCi) was added into 0.1 M ammonium citrate buffer (0.1 mL, pH 5.5) and the anti-miR-712-DOTA (1 mM, 3-4 μL) in double distilled water was slowly added. After incubation for 1 hour at 40° C., the pH was adjusted to 7 by 1 M sodium hydroxide solution (trace metal, Aldrich). The reaction mixture was aspirated into 5 mL TEAA (10 mM, pH 7.0-7.5) in a 10 mL syringe. The solution was slowly eluted through a Sep-Pak light C18 cartridge (Waters, Milford, Mass.) prewashed by methanol and 10 mM TEAA. The C18 cartridge was washed with 10 mM TEAA (4 mL) two times and eluted by 95% methanol (0.5-0.8 mL) to release the radiolabeled product into a 2-mL tube. The solvent was evaporated to dryness with a gentle stream of nitrogen gas at 40° C. Isolated $^{64}$Cu-labeled anti-miR-712-DOTA was dissolved in a phosphate buffered-saline (0.2 mL). Concentrated solution was diluted with PBS to prepare a dose of ~0.2-0.3 mCi/150 μL, which was filtered through 0.2 μm of a Whatman Anotop syringe filter (Dassel, Germany). The specific activity of $^{64}$Cu-anti-miR-712-DOTA was ~500-750 mCi/μmol. Radiochemical purity measured by a binary pump HPLC system (Waters), was more than 95%.

Isolation of Endothelial-Enriched RNA from the LC and GC Regions of the Mouse Aortic Arch Ascending aortas were harvested from C57BL/6 mice and opened en face. The endogenous d-flow region (lesser curvature; LC) and s-flow regions (greater curvature; GC) were identified and carefully dissected out. The endothelium was placed against a nitrocellulose-membrane soaked in isopropanol for 5 minutes, and the media and adventitia were peeled away leaving the endothelial monolayer adherent to the nitrocellulose membrane. The nitrocellulose membrane was then used to extract the miRNA using Qiagen miREasy kit. The left over adventitia samples were visualized under microscope to ensure that the endothelial layer was properly transferred onto the nitrocellulose membrane. For each experiment, LC and GC regions from two to four mice were pooled. A panel of markers genes for endothelium (PECAM1), smooth muscle (aSMA) and immune cell (CD11b) was used to determine the enrichment of endothelial RNA from the preparation.

Ang II Induced miR-712 Expression In Vivo and In Vitro

Figure 9A:
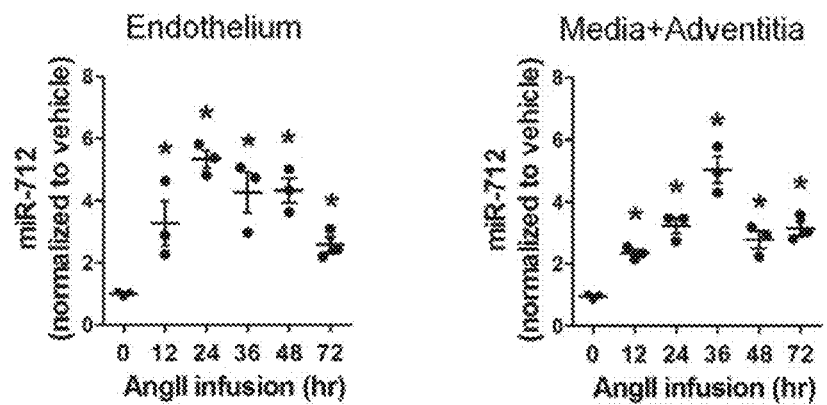
FIG. 9A shows data where expression of miR-712 was determined by qPCR using endothelial-enriched RNA from AngII-infused abdominal aorta and leftover RNA (media/adventitia) obtained from AngII-infused C57BL/6 mouse (0-72 hr).
Figure 9B:
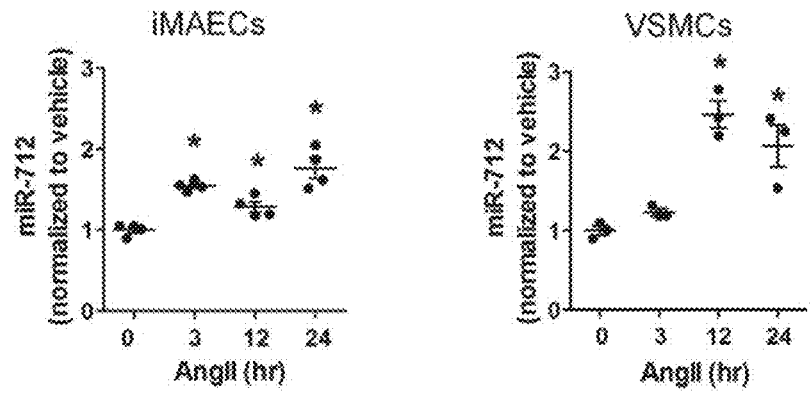
FIG. 9B shows data where miR-712 expression was tested in immortalized mouse aortic endothelial cells (iMAECs) and vascular smooth muscle cells (VSMC) in vitro (0-24 hr). (Data were analyzed using ANOVA followed by Tukey's post hoc test, mean±S.E. *p<0.05; n=4).
Figure 9C:
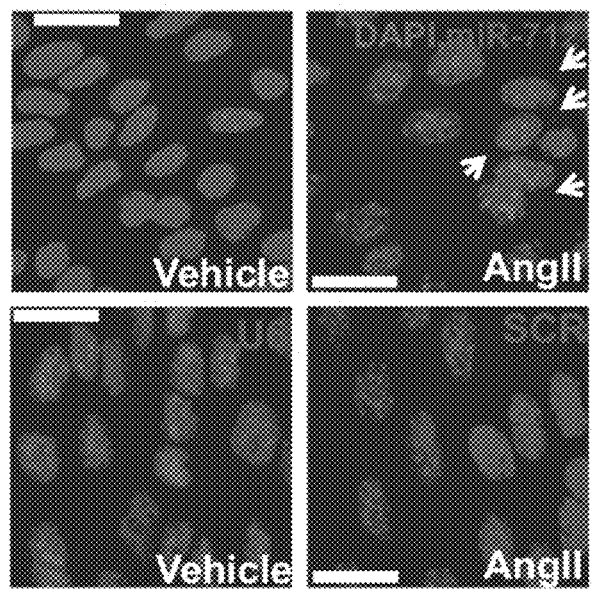
FIG. 9C shows abdominal aortas of C57BL/6 mice obtained at 2-days post AngII-infusion were subjected to fluorescence in situ hybridization using digoxigenin-labeled miR-712 probe and confocal microscopy, (n=4). DAPI nuclear stain; Arrows indicate cytosolic miR-712.

A time-dependent miR-712 expression was tested in AngII infused abdominal aortic endothelium as well as the leftover sample (containing RNAs of medial smooth muscle cells and adventitial cells). AngII infusion increased miR-712 expression between 12-72 h time-points in both the endothelial and media/adventitia samples (FIG. 9a). AngII treatment induced miR-712 expression in both iMAECs and VSMCs in vitro (FIG. 9b). Next, in situ hybridization was performed to further validate the AngII-sensitivity of miR-712 expression in the abdominal aortic endothelium. Studies using in situ hybridization with a miR-712 probe (Exiqon) showed a robust expression of miR-712 in the cytoplasm (arrows) and nuclei of the abdominal aortic endothelium, compared to the vehicle (FIG. 9c). These results suggest that AngII treatment increases miR-712 expression both in endothelial cells and smooth muscle cells in the mouse abdominal aorta in vivo as well as in vitro.

TIMP3 and RECK are Direct Targets of miR-712

Figure 10A:
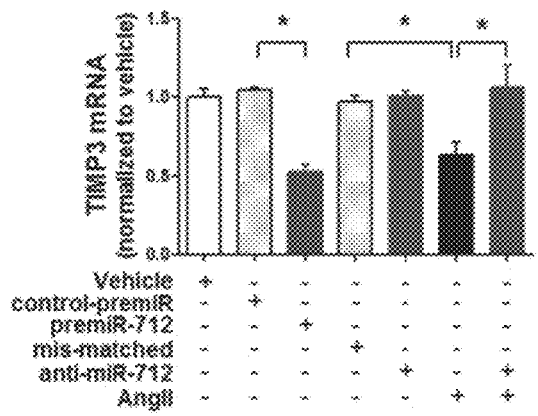
FIG. 10A shows data where TIMP3 expression were determined by qPCR in iMAECs treated with AngII (100 ng/ml) and pre-miR-712 (20 nM) with or without anti-miR-712 (400 nM) (n=4; p<0.05).
Figure 10B:
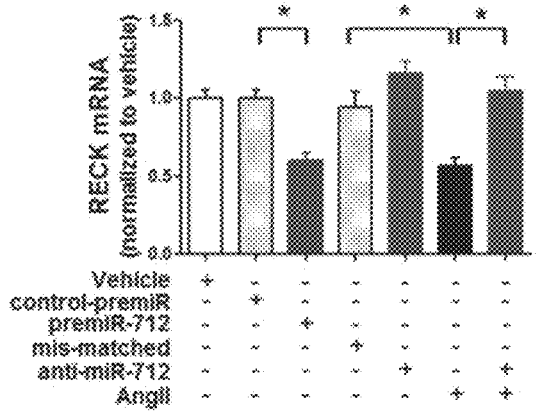
FIG. 10B shows data for RECK.
Figure 10C:
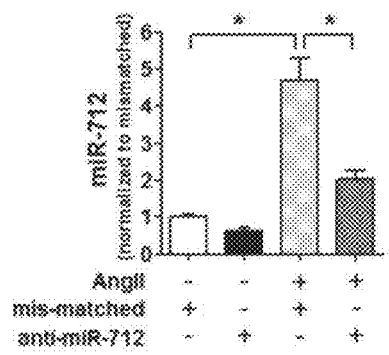
FIG. 10C shows data where endothelial-enriched RNAs were prepared from suprarenal artery of AngII (1 µg/kg/min)-infused mice, which were injected with mis-matched control or anti-miR-712 (5 mg/kg; injected subcutaneously, s.c.) twice (one and two days before AngII infusion). miR-712, expression was determined by qPCR. (n=4; p<0.05).
Figure 10D:
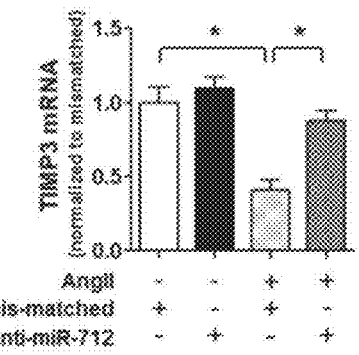
FIG. 10D shows data for TIMP3.
Figure 10E:
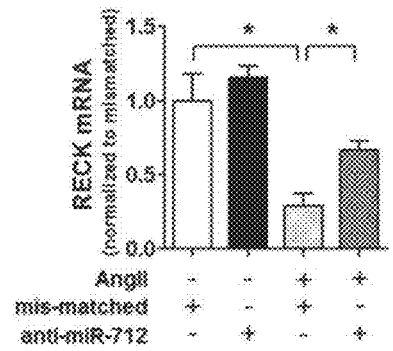
FIG. 10E shows data for RECK.

Through in silico analysis using TargetScan, an additional potential target of miR-712, RECK was identified in response to the humoral AngII stimulation. Since TIMP3 and RECK are well-known negative regulators of MMP activity, a critical player in AAA development and progression, we examined whether miR-712 indeed targeted TIMP3 and RECK expression using gain-of-function (premiR-712) and loss-of-function (anti-miR-712) approaches in the AngII-dependent manner. Treatment with premiR-712 and AngII significantly decreased TIMP3 and RECK mRNA expression, both of which were blocked by anti-miR-712 treatment in iMAEC (FIGS. 10a and 10b) in vitro. In addition, AngII-stimulated miR-712 induction as well as downregulation of TIMP3 and RECK were significantly reversed in mice treated with anti-miR-712 (FIGS. 10d and 10e). For this study, anti-miR-712 was subcutaneously injected twice (1 and 2 days prior to AngII implantation) at 5 mg/kg/day dose, and effectively silenced AngII-induced miR-712 expression (FIG. 10c).

Figure 10F:
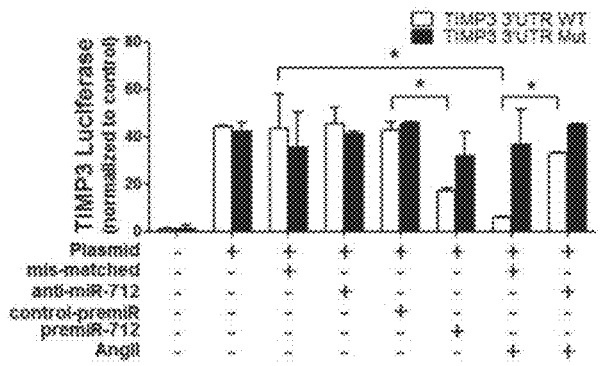
FIG. 10F shows data where iMAECs transfected with dual-luciferase reporter plasmids containing wild-type (WT) or mutant (Mut) of TIMP3-3'UTR were treated with AngII (100 ng/ml), pre-miR-712 (20 nM) or control pre-miR (20 nM) and anti-miR-712 (400 nM). Firefly luciferase activity (normalized to control Renilla luciferase) indicating TIMP3 expression was determined using Luc-Pair miR Luciferase Assay Kit.
Figure 10G:
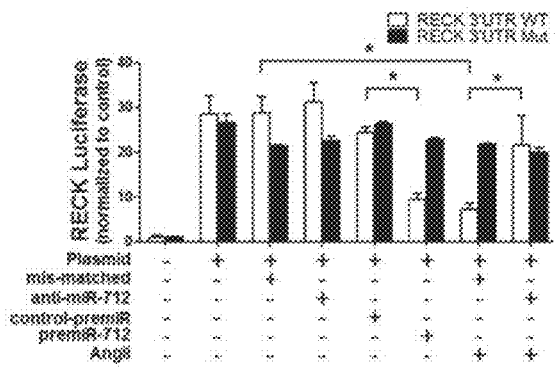
FIG. 10G shows data for RECK-3'UTR.

To further determine whether miR-712 bound to and inhibited TIMP3 and RECK expression directly in an AngII-dependent manner, we performed the luciferase assay, in which a construct containing the 3'-UTR region of TIMP3 or RECK mRNA containing the putative miR-712 binding sequence was used. Treatment of iMAECs with premiR-712 and AngII inhibited luciferase activity of TIMP3 and RECK, while their mutants or control-premiR showed no effect (FIGS. 10f and 10g). In addition, anti-miR-712 blocked the inhibitory effect of premiR-712 or AngII on TIMP3 and RECK luciferase activity (FIGS. 10f and 10g). Together, these data suggest that TIMP3 and RECK are direct targets of miR-712 in response to AngII.

Figure 10H:
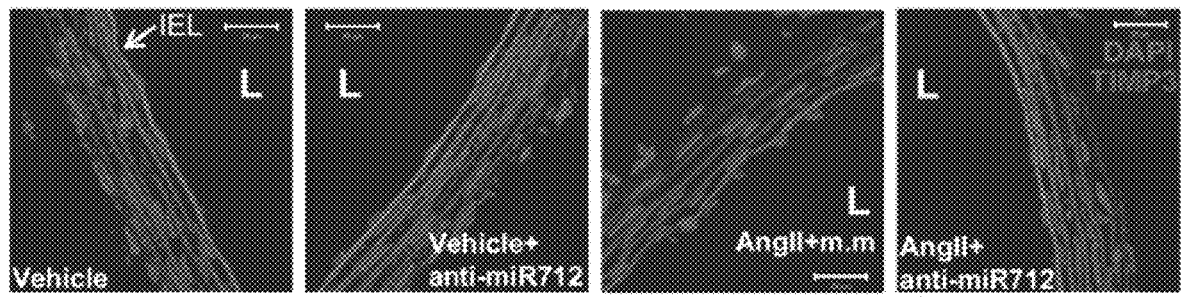
FIG. 10H shows data on frozen sections of abdominal aortas obtained from AngII-infused C57BL/6 mice were used for immunofluorescence staining with antibody specific to TIMP3.
Figure 10I:
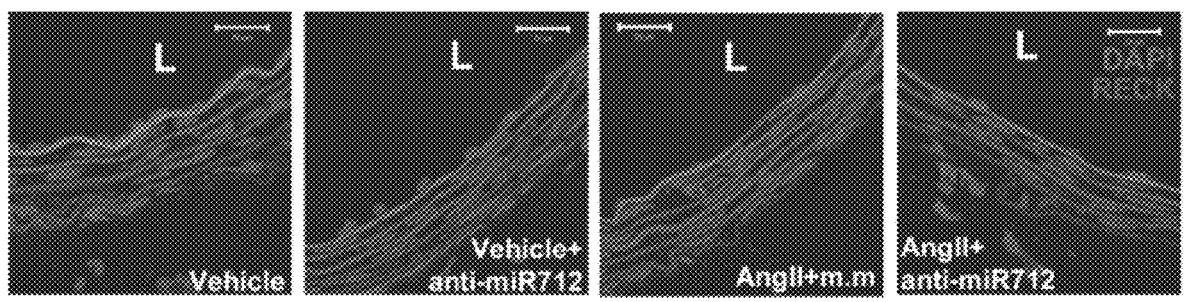
FIG. 10I shows data for antibody specific to TIMP3.
Figure 10J:
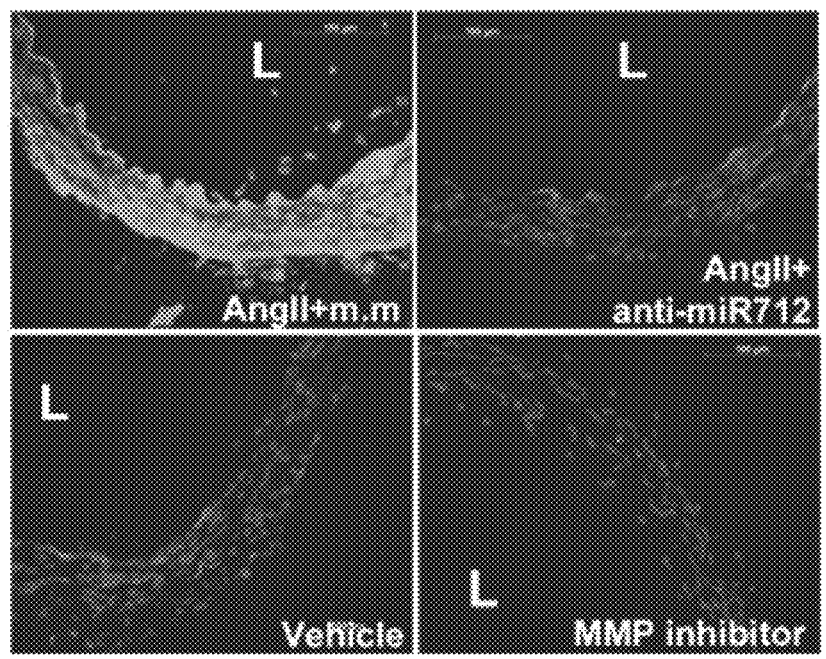
FIG. 10J shows data in situ zymography where some abdominal aorta sections were incubated with the MMP inhibitor GM6001 (right bottom panel; scale bar=100 µm).
Figure 10K:
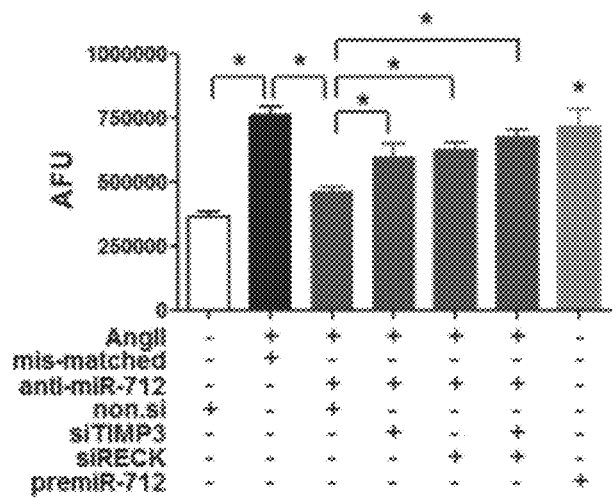
FIG. 10K shows data where iMAECs, pretreated with AngII (100 ng/ml) and/or premiR-712 (20 nM) for 1 day, were further treated with anti-miR-712 or mismatched control at 400 nM each as well as siRNAs against TIMP3 and RECK (siRECK or siTIMP3), respectively, at 100 nM each for 1 day. MMP activity was determined by cell-based ELISA using DQ-gelatin.

Whether AngII downregulates TIMP3 and RECK expression by a miR-712-dependent mechanism in vivo was tested by immunostaining. Expression of TIMP3 and RECK were evident in endothelial and smooth muscle cells in the vehicle control groups (FIGS. 10h and 10i). AngII infusion decreased the expression of TIMP3 and RECK compared to the vehicle, but anti-miR-712 treatment reversed it (FIGS. 10h and 10i). Since TIMP3 and RECK are well-known inhibitors of MMPs, we examined the effect of anti-miR-712 on MMP activity in vivo by using an in situ zymography assay using the fluorescent DQ-gelatin. As shown in FIG. 10j, AngII infusion increased MMP activity as evidenced by the green fluorescent signal intensity, but was prevented by treating mice with anti-miR-712 in vivo or the MMP inhibitor GM6001 added during the zymography assay. This in situ zymography result was further confirmed in an in vitro cell-based assay using iMAEC (FIG. 10k). The in vitro study showed that AngII induced MMP activity, which was prevented by anti-miR-712 treatment.

Whether TIMP3 or RECK, or both were important player in regulation of the AngII-dependent MMP activity was investigated. For this study, cells pre-treated with AngII and anti-miR-712 were treated with siRNAs to knockdown TIMP3, RECK, or both. The inhibitory anti-miR-712 effect on the MMP activity was partially blunted when cells were treated with TIMP3 siRNA or RECK siRNA (FIG. 10k). Interestingly, knockdown of both TIMP3 and RECK together did not produce the additive effect, which may be due to an insensitive assay condition or an unknown cooperation between the two inhibitors. Together, these results demonstrate that AngII stimulates MMP activity by inducing expression of miR-712, which in turn downregulates TIMP3 and RECK, both of which seem to be equally important in MMP activity regulation.

Anti-miR-712 Inhibits AAA Induced by AngII Infusion

Figure 11A:
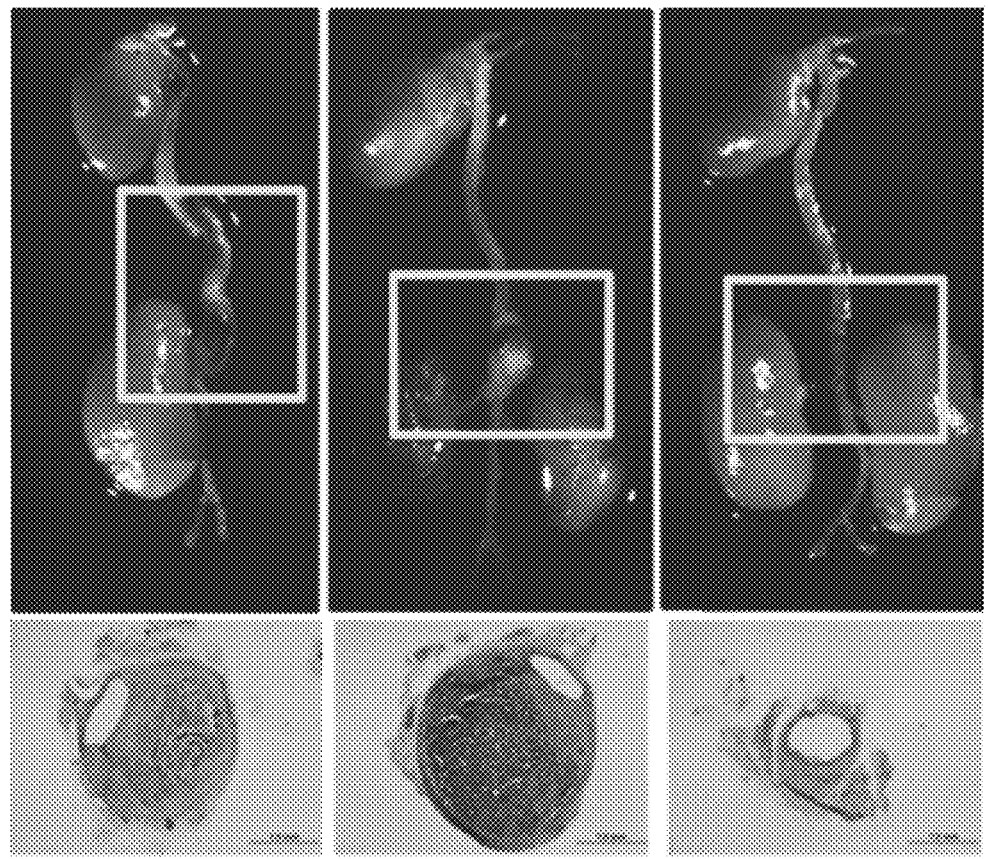
FIG. 11A shows data where ApoE$^{-/-}$ mice (24-26 weeks) were infused with AngII (1 µg/kg/min) or saline for 3 weeks via osmotic minipump and were injected with mis-matched control (5 mg/kg) or anti-miR-712 (5 mg/kg). ApoE$^{-/-}$ mice (24-26 weeks) were infused with AngII (1 µg/kg/min) or saline for 3 weeks via osmotic minipump and were injected with mis-matched control (5 mg/kg) or anti-miR-712 (5 mg/kg). Photographs showing macroscopic features of aneurysms induced by AngII. The square shows typical AAAs in ApoE$^{-/-}$ mice. Lower panel shows representative H&E staining for each group.
Figure 11B:
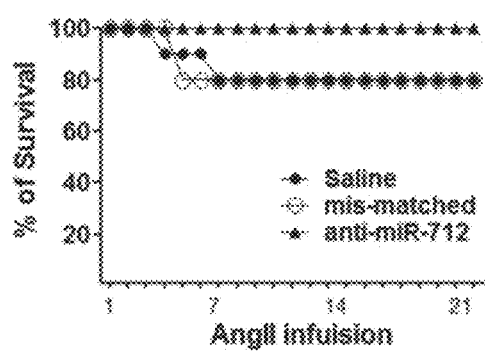
FIG. 11B shows data on the survival in anti-mR-712 treated group compared to saline or mis-matched anti-miR controls (n=10).
Figure 11C:
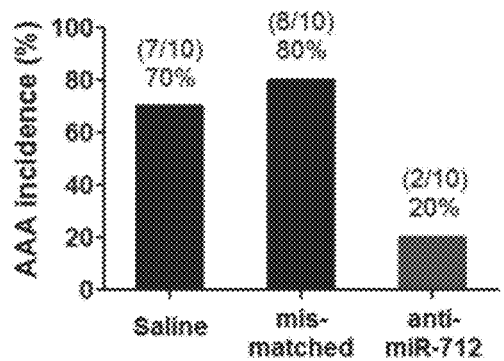
FIG. 11C shows data on incidence rate of AngII-induced AAA.
Figure 11D:
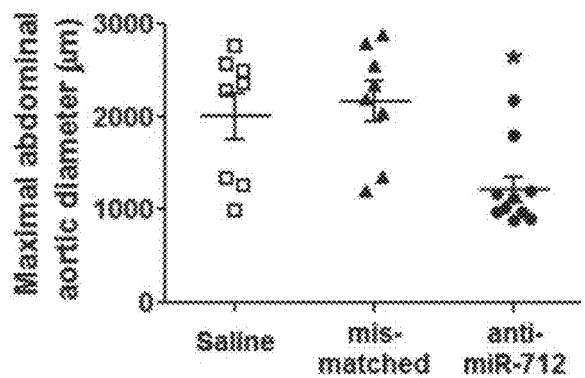
FIG. 11D shows data on the maximal abdominal aortic diameter quantitated using the H&E stained section; compared to saline or mis-match control group. The data was analyzed using the Kruskal-Wallis test followed by the Mann-Whitney U-test using Bonferroni correction to adjust the probability (*p<0.05; n=10 each group).

Whether anti-miR-712 can prevent AAA induced by AngII infusion in ApoE$^{-/-}$ mice was tested using the Daugherty method. For this study, mice were treated with anti-miR-712 using the same dosage and protocol used above in FIG. 10c-e, except for additional anti-miR-712 injections every 4 days for 3 weeks following AngII implantation. AngII infusion (1 μg/kg/min) for 3 weeks induced pronounced AAA phenotype in the suprarenal region of the abdominal aorta, which was significantly blunted in the anti-miR-712-treated mice compared to the mis-matched or saline-treated control groups (FIG. 11a). While 20% (2 out of 10 mice each) of AngII-infused mice died during the first week in the saline and mis-matched groups, none of the anti-miR-712 treated mice showed mortality for the duration of the study (FIG. 11b). Also, treatment with anti-miR-712 dramatically reduced AAA incidence to 20% (2 of 10 mice) compared to the mis-matched (80%; 8/10) or saline controls (70%; 7/10) (FIG. 11c). Similarly, the increase in AngII-induced abdominal aortic diameter was also significantly reduced by the anti-miR-712 treatment compared to the saline and mis-matched controls (FIG. 11d).

Figure 11E:
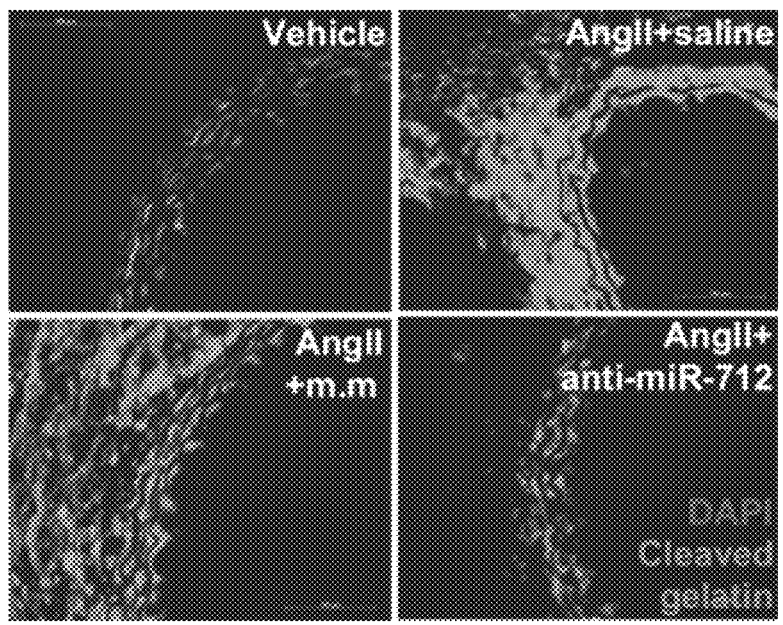
FIG. 11E shows in situ zymography using DQ-gelatin to determine MMP activity in AngII-infused abdominal aortic sections with saline, mis-matched control or anti-miR-712 injected group (scale bar=100 µm).

Whether anti-miR-712 could inhibit AngII-induced MMP activity was tested by the in situ zymography using DQ-gelatin. The MMP activity (shown as the intense fluorescent gelatin signal) was dramatically higher in AngII-infused mice (AngII+saline group) compared to the vehicle control, but it was remarkably reduced in the anti-miR-712-treated mice compared to the mis-matched control (FIG. 11e).

Figure 11F:
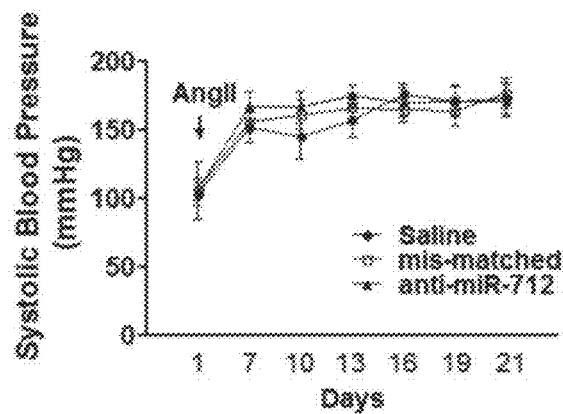
FIG. 11F shows systolic blood pressure measured in AngII-infused mice treated with anti-miR-712 compared to saline or mis-matched controls (n=10 each group).
Figure 11G:
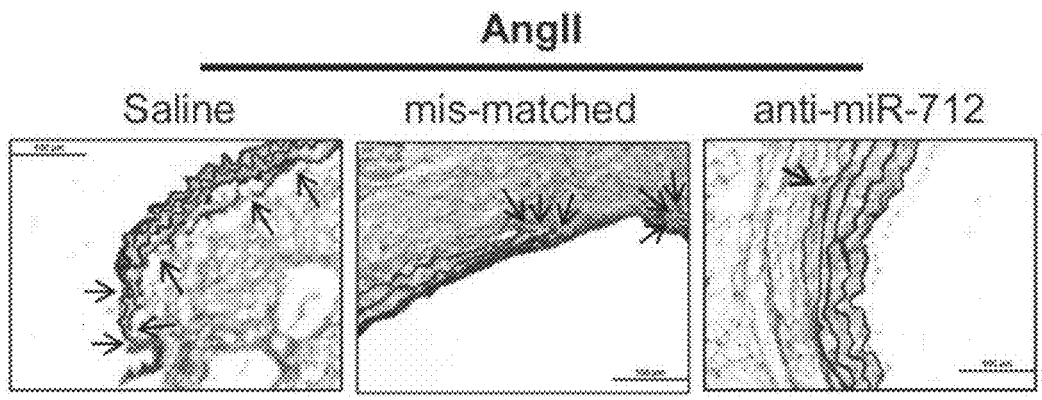
FIG. 11G shows data where elastin fragmentation was evaluated by histochemical staining with Orcein elastin stain kit using aorta sections of saline, mis-matched control and anti-miR-712 treated groups.
Figure 11H:
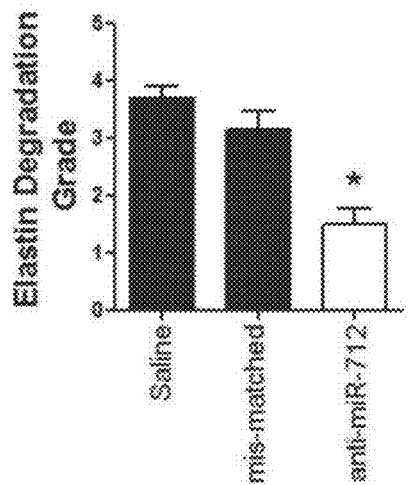
FIG. 11H shows quantitation of elastin degradation. The data was analyzed using the Kruskal-Wallis test followed by the Mann-Whitney U-test using Bonferroni correction to adjust the probability (*p<0.05; n=6 each group).

Whether the anti-AAA effect of anti-miR-712 was mediated through normalizing blood pressure was testeom in the AngII-infused mice. AngII-infusion significantly increased blood pressure within one week following the AngII infusion, but anti-miR-712 treatment did not alter the blood pressure (FIG. 11f). Aortic wall elastin fragmentation is an important feature of AAA in both humans and mouse models. The elastic lamina degradation were graded on a scale of 1 (least) to 4 (worst) in our mouse samples. The elastic laminas were frequently disrupted and fragmented in AngII-infused mice treated with saline or mis-matched controls, whereas anti-miR-712 treated mice showed little signs of elastin fragmentation (FIGS. 11g and 11h). These results suggest that the anti-AAA effect of anti-miR-712 is mediated in an MMP-dependent manner, but is independent of the pressor response.

Anti-miR-712 Inhibits Both Endothelial and Circulating Leukocyte Inflammation

Figure 4A:
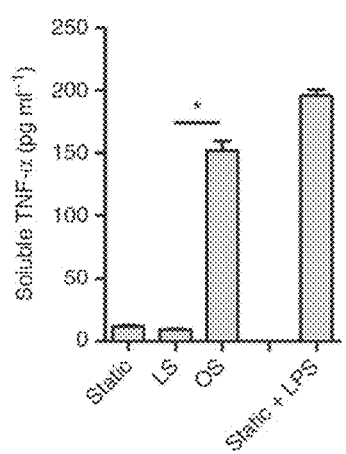
FIG. 4A shows data where iMAECs were exposed to static, LS or OS for 24 h, and the conditioned media were used for TNFa enzyme-linked immunosorbent assay (ELISA). LPS was used as a positive control.
Figure 4B:
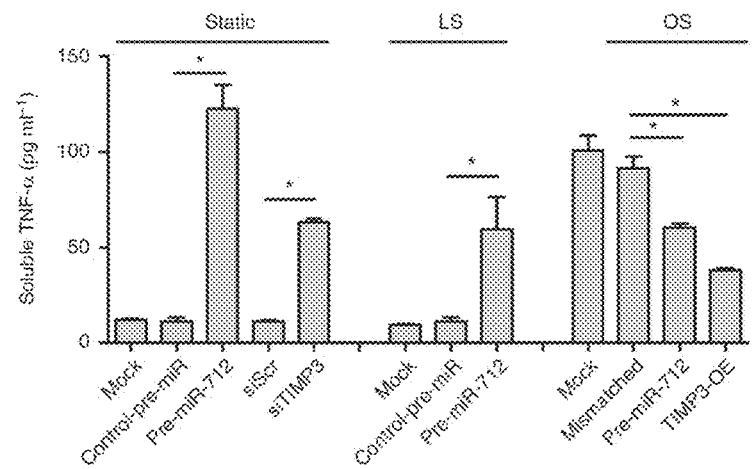
FIG. 4B shows data where iMAECs were transfected with TIMP3 expression vector (TIMP3-OE), TIMP3 siRNA (150 nM), pre-miR-712 (20 nM), anti-miR-712 (400 nM) and respective controls for 24 h. Cells were then exposed to static, LS or OS for 24 h, and s-TNFα in conditioned media was determined by ELISA. (n=6, data shown as mean±s.e.m.; *p<0.05 as determined by one-way analysis of variance (ANOVA).
Figure 5C:
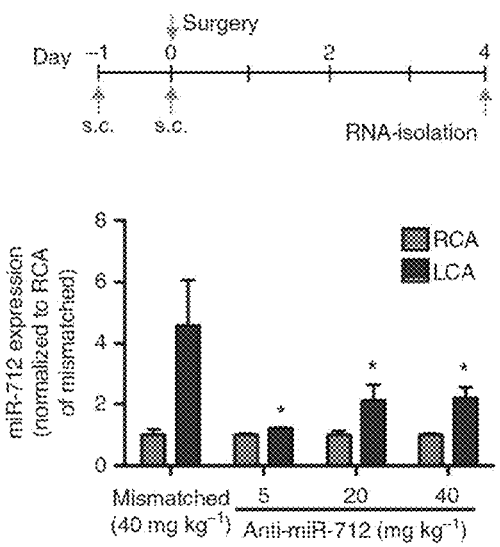
FIG. 5C shows date used to determine the optimal dose of anti-miR-712, C57B16 mice were injected with anti-miR-712 daily for 2 days (s.c. at 5, 20 or 40 mgkg$^{-1}$ per day) and followed by partial carotid ligation. Mismatched anti-miR-712 (40 mg kg$^{-1}$ per day) was used as a control. Endothelial-enriched RNAs were prepared from LCA and RCA obtained at 4 days post ligation, and miR-712 expression was determined by qPCR showing optimal effect at 5 mg kg$^{-1}$ dose (n=4 each, data shown as mean±s.e.m.; *p<0.05 as determined by paired t-test).
Figures 5D, 5E, 5F:
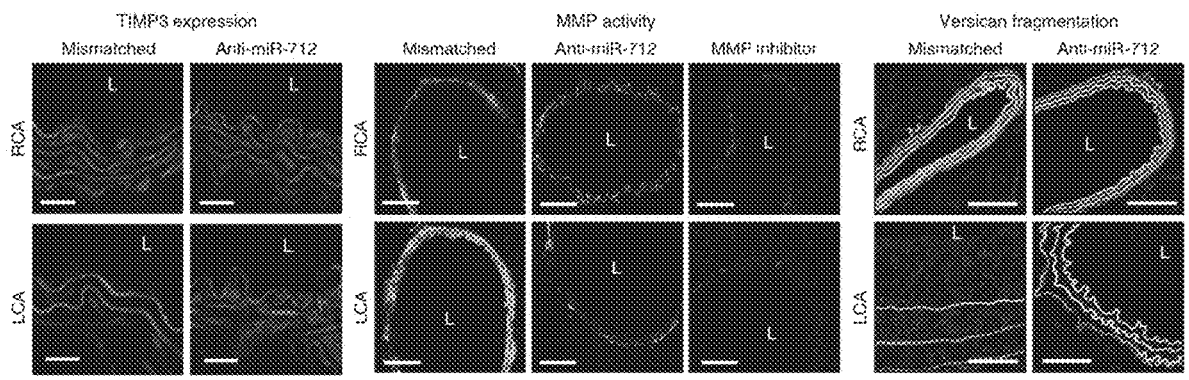
FIG. 5D shows data where ApoE$^{-/-}$ mice were partially ligated and fed HFD for 1 week. RCA and LCA frozen sections obtained from these mice were used for immunofluorescence staining with antibody specific to TIMP3 (scale bar, 20 mm).
FIG. 5F shows data for two weeks using versican fragment peptide DPEAAE (scale bar, 20 mm)
FIG. 5E shows date of in situ zymography using DQ-gelatin to determine MMP activity. As a control for the MMP activity assay, some LCA and RCA sections were incubated with MMP inhibitor 1. DAPI and autofluorescent elastic lamina (L=lumen of the artery). Scale bar, 50 μm.
Figure 6A:
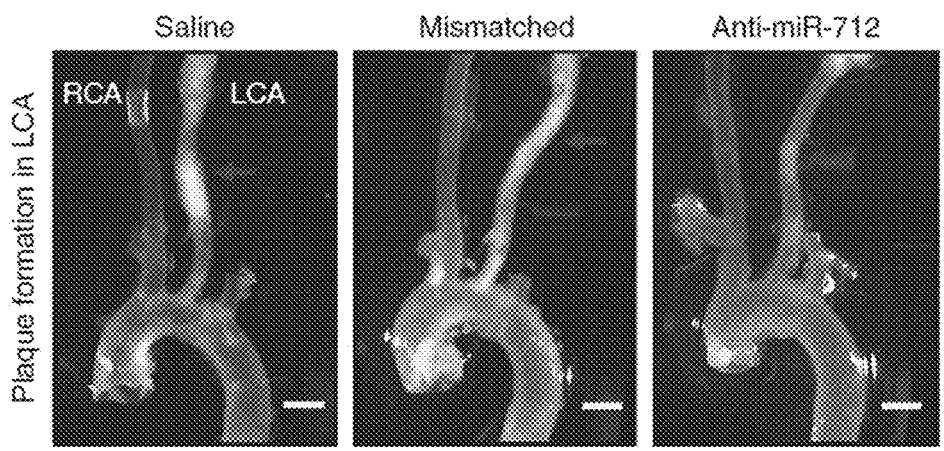
FIG. 6A shows data where ApoE−/− mice were pretreated twice with anti-miR-712 or mismatched control (5 mg·kg$^{-1}$ each, s.c.) or saline on 1 and 2 days before partial ligation. Mice were then fed a HFD and anti-miR and control treatments were continued (twice a week s.c.) for 2 weeks. Aortic trees including the carotids were dissected and examined by bright field imaging and lesion area was quantified (n=10 each, data shown as mean±s.e.m.; *p<0.05 as determined by one-way analysis of variance (ANOVA). Scale bar, 1 mm.
Figure 7B:
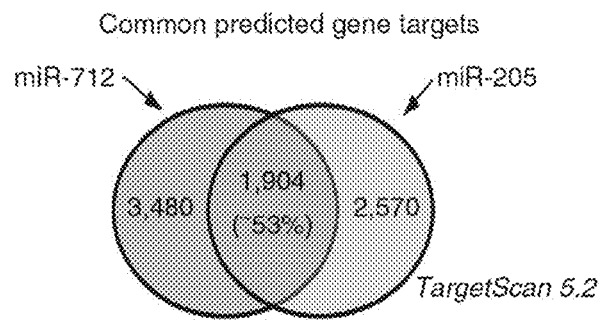
FIG. 7B shows putative targets of miR-712 and miR-205 obtained from TargetScan were compared. Venn diagram depicts the common gene targets of miR-205 and miR-712.
Figure 7C:
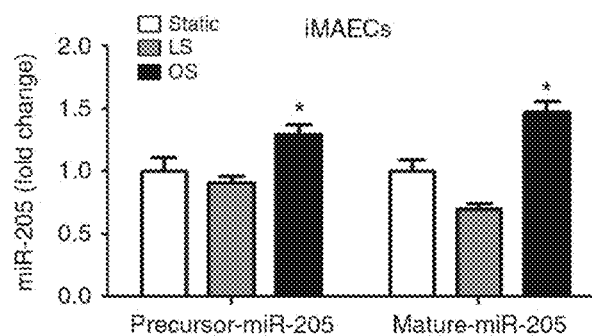
FIG. 7C shows data where expression of precursor and mature miR-205 in iMAECs were exposed to static, LS or OS for 24 h (n=4; data shown as means±s.e.m.; *p<0.05 as determined by Student's t-test).
Figure 7D:
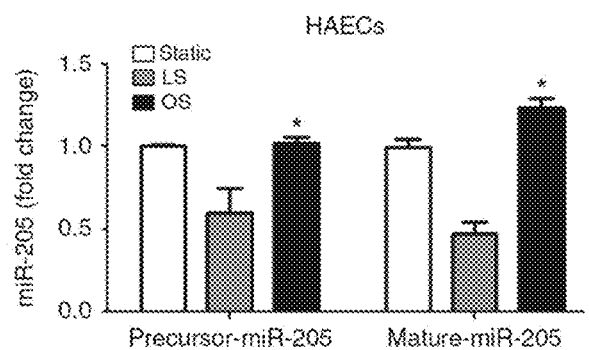
FIG. 7D shows data where expression of precursor and mature miR-205 in human aortic endothelial cells (HAECs) were exposed to static, LS or OS for 24 h (n=4; data shown as means s.e.m.; *p<0.05 as determined by Student's t-test).
Figure 7E:
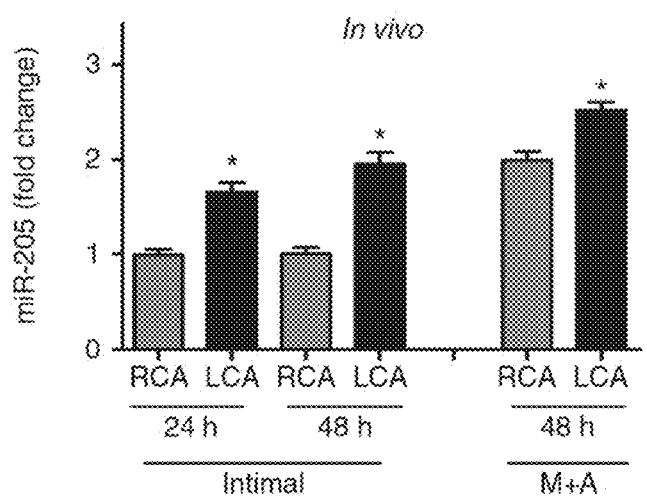
FIG. 7E shows data where expression of mature miR-205 was determined using the RNAs obtained from the endothelial-enriched (intimal region) and the leftover medial and adventitia region (M+A) of the LCA and RCA at 24 and 48 h post partial ligation, respectively.
Figure 12A:
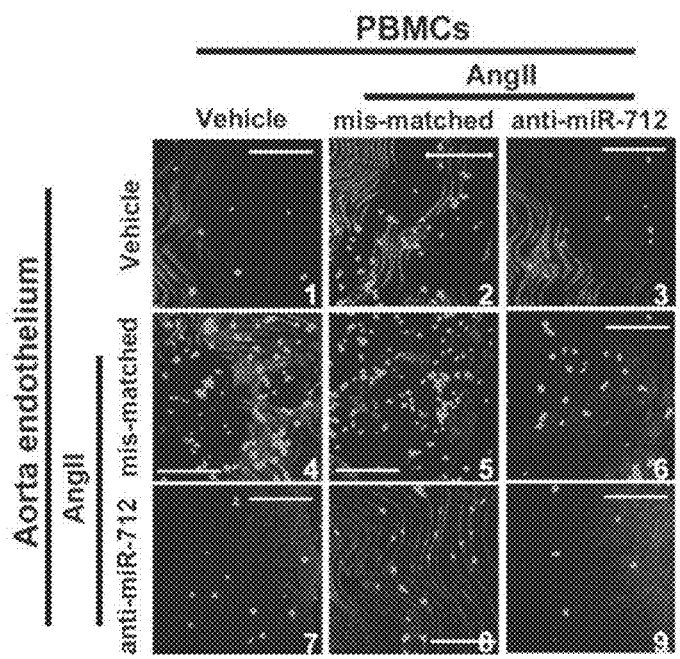
FIG. 12A shows data indicating injection of anti-miR-712 affects both immune cells and vessel wall cells, which in turn inhibit PBMCs adhesion to endothelium of suprarenal artery.
Figure 12B:
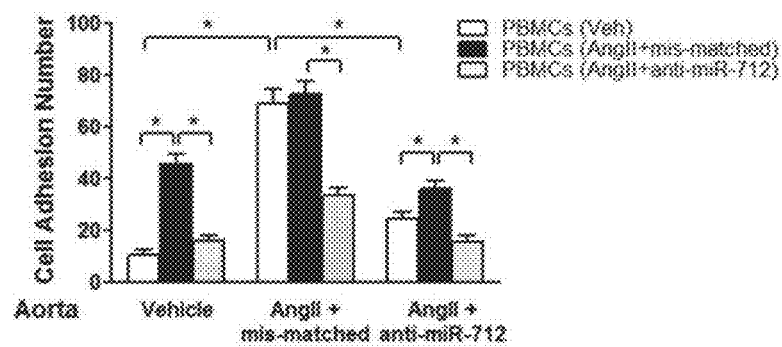
FIG. 12B shows data where abdominal aortic explants as well as PBMCs were obtained from vehicle or AngII-infused (1 µg/kg/min; 2 days) C57BL/6 mice that were also treated with mis-matched or anti-miR-712 (5 mg/kg, s.c; 2 daily injections prior to AngII implantation). PBMCs (labeled with fluorescent Calcein) were then incubated for 30 min with the abdominal aortic explants with their endothelial side up, and the PBMCs adhered to the endothelial surface was counted by confocal microscopy.
Figure 12C:
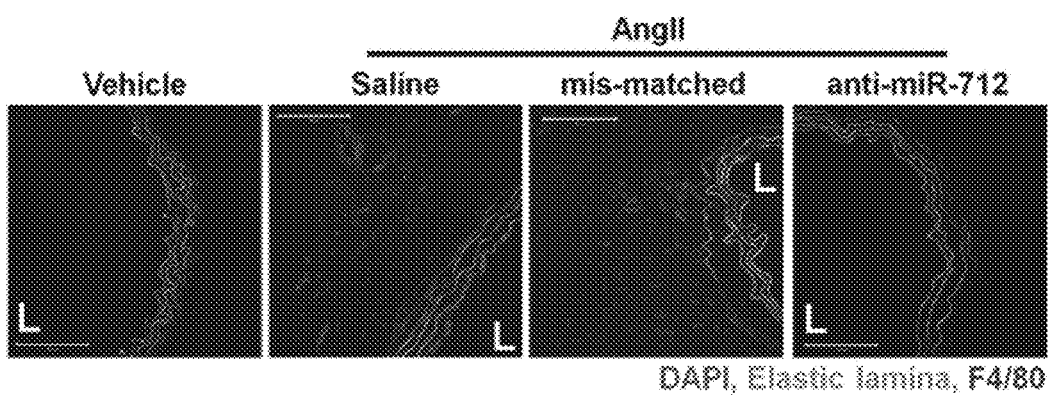
FIG. 12C shows data where macrophage (F4/80$^+$) infiltration was examined by the immunostaining the abdominal aorta section obtained in the frozen sections described in FIG. 3D (scale bar, 100 µm; n=5 each group).

Given the importance of inflammation in AAA development, whether the effect of anti-miR-712 (delivered systemically via s.c. injection) was mediated through the aortic endothelial cells, circulating leukocytes or both was examined. To test this hypothesis, an ex vivo leukocyte adhesion assay was performed using abdominal aorta explants and peripheral blood monocytic cells (PBMCs) obtained from the mice treated with anti-miR-712 or mis-matched control along with vehicle or AngII-infusion. Three groups of aortas were obtained from the mice that were treated with 1) vehicle, 2) AngII+mis-matched control, or 3) AngII+anti-miR-712. In addition, PBMCs were also obtained from the same three groups of mice as above. These 3 groups of aortic explants and 3 groups of PBMCs were then used in a 3×3 combination study (FIG. 12a). Here, PBMCs were added to an aortic explant with its endothelial surface up in a dish, and the number of PBMCs adhering to the endothelial surface after a 30 min incubation time was microscopically quantitated. First, adhesion of vehicle-control PBMCs to the vehicle-control endothelial surface was very low (FIG. 12a, panel 1). Second, both PBMCs and aortic explants obtained from AngII-infused mice showed significantly increased adhesion as compared to the vehicle control (as indicated by the increased number of PBMCs shown as green dots) (FIG. 11a: panel 1 vs. 2; panel 1 vs. 4). Third, both the aorta explants and PBMCs obtained from anti-miR-712 treated mice showed a significant reduction in PBMC adhesion to endothelium compared to the mis-matched controls (FIG. 11a: panel 3 vs. 2; panel 7 vs. 4), suggesting the anti-inflammatory effect of anti-miR-712 treatment. The quantitative results shown in FIG. 4B further supported these points. Consistent with these ex vivo results, we also found a robust F4/80$^+$ monocyte/macrophage staining in AngII-infused mice with saline or mis-matched controls, but it became nearly undetectable in the anti-miR-712 treated mice (FIG. 11c). These findings suggest that the anti-AAA effect of anti-miR-712 is mediated, at least in part, by inhibiting inflammation of both aortic endothelial cells and circulating leukocytes.

The miR-205, a Human Homolog of miR-712, Directly Targets TIMP3 and RECK

Figure 13A:
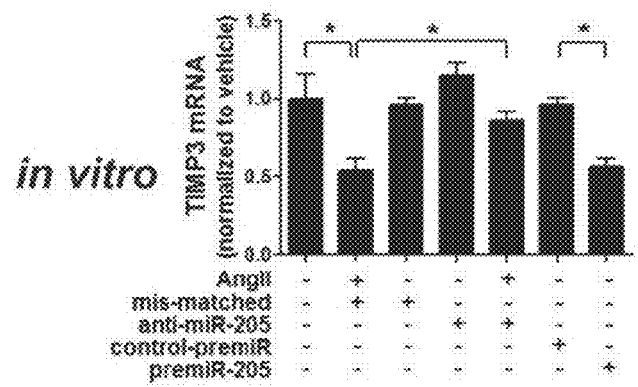
FIG. 13A shows data where TIMP3 expression was determined by qPCR in iMAECs pre-treated with premiR-205 (20 nM), anti-miR-205 (400 nM) or mis-matched control (400 nM) for 2 days, followed by AngII (100 ng/ml) treatment for another 1 day (n=4; *p<0.05; in triplicate).
Figure 13B:
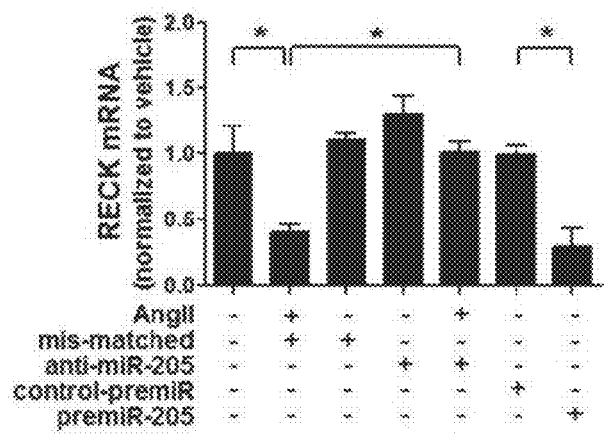
FIG. 13B shows data for RECK.
Figure 13C:
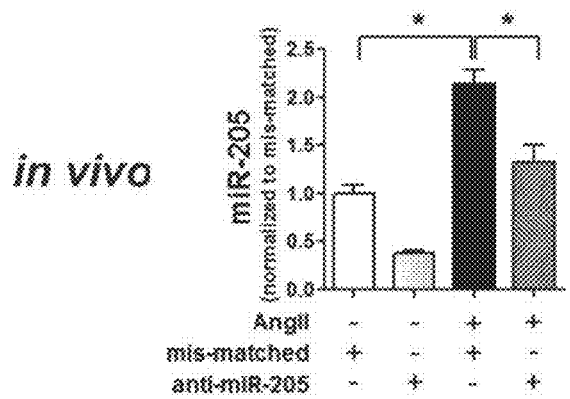
FIG. 13C shows data where endothelial-enriched RNAs were prepared from the abdominal aortas of vehicle or AngII-infused mice, which were pre-treated with mis-matched control or anti-miR-205 (5 mg/kg; 2 daily injections), and miR-205 expression was determined by qPCR (n=4; *p<0.05; in triplicate). All data were analyzed using ANOVA followed by Tukey's post hoc test, and values represent the mean±S.E.

Since miR-712 is murine-specific, its clinical implication for human disease could be limited. To address this potential concern, its potential human homolog, miR-205, was identified which shares the 7-mer "seed sequence" with miR-712 and is highly conserved in most mammalian species (TargetScan) including mouse and human. Whether miR-205 also targets TIMP3 and RECK in endothelial cells in an AngII-dependent manner by using a gain-of-function (premiR-205) and loss-of-function (anti-miR-205) approaches was tested. Treatment of iMAEC with premiR-205 or AngII decreased TIMP3 and RECK mRNA expression, which was prevented by anti-miR-205 treatment (FIGS. 13a and 13b). Similarly, AngII treatment increased expression of miR-205 in mouse aortic endothelium and the media+adventitial cells in vivo (FIG. 13c). AngII-induced miR-205 expression was effectively silenced by anti-miR-205 treatment in mice (FIG. 13c), using the same dosage and injection protocol used for anti-miR-712 (FIG. 13c-e). AngII treatment decreased TIMP3 and RECK expression, which was reversed by anti-miR-205 treatment in mouse aortic endothelium (FIGS. 13d and 13e). These results suggest that miR-205 expression is AngII-sensitive and it targets TIMP3 and RECK, like miR-712.

Treatment with Anti-miR-205 Prevents Ang II-Induced AAA

Figure 14D:
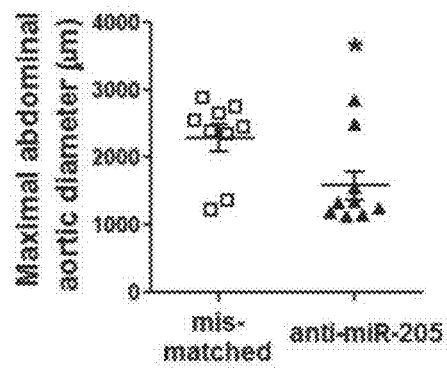
FIG. 14D shows data where maximal abdominal aortic diameter was quantitated using the H&E stained section. The data was analyzed using the Kruskal-Wallis test followed by the Mann-Whitney U-test using Bonferroni correction to adjust the probability (*p<0.05 compared to mis-matched control, n=9 each group).
Figure 14E:
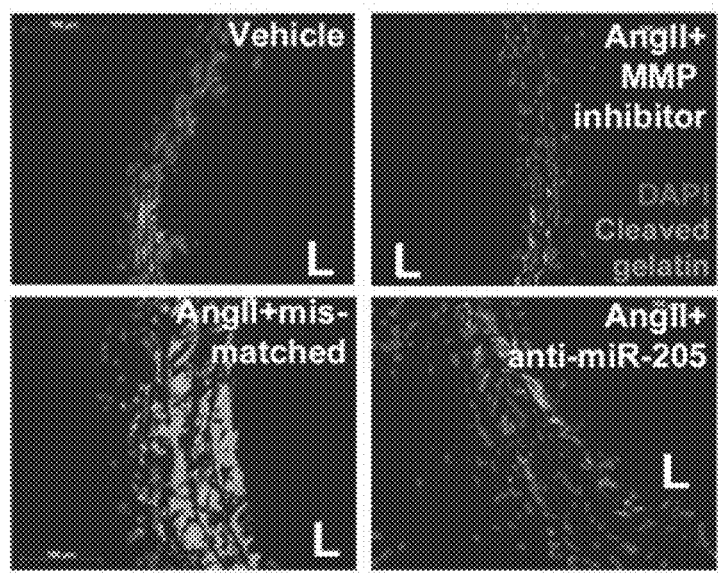
FIG. 14E shows in situ zymography using DQ-gelatin to determine MMP activity in vehicle or AngII-infused abdominal aortic sections with mis-matched control or anti-miR-205 treated group (n=4, scale bar=100 µm). Some sections from the AngII+mis-matched control treated mice were incubated with GM6001 (upper right panel).
Figure 14F:
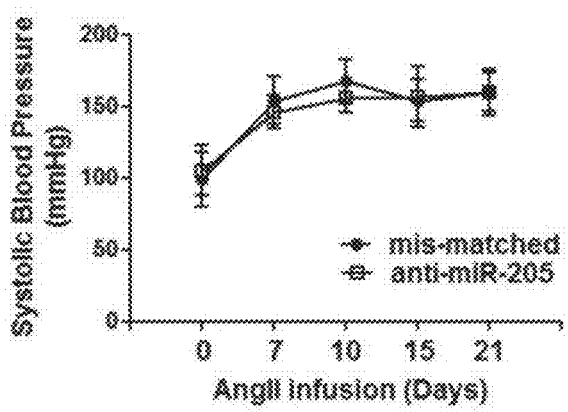
FIG. 14F shows systolic blood pressure measured in AngII-infused mice treated with anti-miR-205 compared to mis-matched controls (n=9).

To determine whether miR-205 plays an important role in AAA, AngII-infused ApoE$^{-/-}$ mice were treated with anti-miR-205 or mis-matched control using the same protocol as anti-miR-712. As shown in FIG. 14a-d, anti-miR-205 treatment significantly decreased AAA incidence, mortality, and abdominal aorta dilation compared to the mis-matched control. While the survival rate of AngII-infused and mis-matched group was 56% (5/9), the anti-miR-205-treated group showed 88.8% survival rate at the 3 week time-point (FIG. 14b). Anti-miR-205 treatment significantly reduced AAA incidence (2/9; 22.2%) compared to the mis-matched group (7/9; 77.7%) (FIG. 14c). Next, the effect of anti-miR-205 treatment on MMP activity was tested in the same groups of mice by in situ zymography. AngII-induced MMP activity was nearly blocked by treating the aorta section of the AngII-treated mice with the MMP inhibitor GM6001 during the in situ zymography assay (FIG. 14e; upper right panel). Anti-miR-205 treatment dramatically reduced the MMP activity compared to the mis-matched control (FIG. 14e). These results suggest that the AngII- and miR-205-sensitive metalloproteinase activity is mostly accounted for by the MMP activity. Like anti-miR-712, anti-miR-205 also did not affect AngII-induced systemic hypertension in these mice (FIG. 14f). Taken together, these results demonstrate that, like anti-miR-712, anti-miR-205 treatment has a potent preventive effect on AAA induced by AngII infusion.

Figure 15:
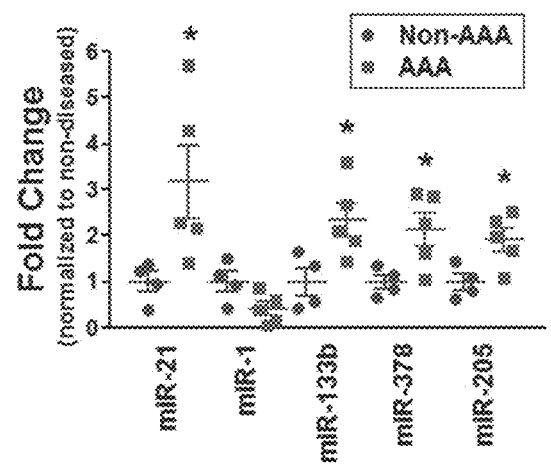
FIG. 15 shows data indicating AngII-sensitive miRNAs expression in human AAA. Expression of AngII-sensitive miRNA; miR-21, miR-1, miR-133b, miR-378 and human homolog of miR-712; miR-205 were determined by qPCR using human normal aorta (n=4) and FFPE sections of human AAA whole tissues (n=5) obtained from Origene. (*p<0.05).

AngII-Sensitive miRNAs in the Murine AAA are Also Upregulated in Human AAA Tissues Whether some of the AngII-sensitive miRNAs identified in this mouse study, including miR-205, -21, -1, 133b and 378 were also upregulated in human AAA tissues was tested. For this study, total RNAs prepared from de-identified human AAA paraffin sections (n=5) were compared to those without the disease (non-AAA, n=4) from Origene. miR-205 expression was ~2-fold higher in AAA samples compared to the non-AAA (FIG. 15). Also, expression of miR-21, miR-133b, and miR-378, but not miR-1, was significantly higher in human AAA samples compared to the non-AAA. This result suggests that miRNAs, especially the human homolog of miR-712, miR-205, identified in our AngII-induced murine AAA model appears to be relevant in human AAA as well.

Anti-miR-205 in the Treatment of Atherosclerosis

Doses (e.g., 200 mg of aqueous solution pH adjustment to 7.5-8.5) of the nucleotide anti-miR205 GCCTCCT-GAACTTCACTCCA (SEQ ID NO: 17) as G*-mC*-mC*-T*-mC*-dmC-dT-dG-dA-dA-dmC-dT-dT-dmC-dA-mC*-T*-mC*-mC*-A*[d=2'-deoxy, *=2'-O-(2-methoxyethyl), mC 5-methylcytidine] are administered by injection repeatedly to a subject. In certain embodiments, it is contemplated that any reverse complement sequence of a twenty nucleotide window of human miR-205 can be used to substitute the nucleotides in the above sequence provided C is 5-methylcytidine.

The invention claimed is:

1. A method of treating or preventing a vascular disease selected from abdominal aortic aneurysm comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUUCUCUU GUCCUUCAUUCCACCGGAGUCUGUCUCAUACC-CAACCAGAUUUCAGUGGAGUGAA GUUCAGGAGG-CAUGGAGCUGACA wherein the nucleobase polymer binds sufficiently to prevent translation of tissue inhibitor of metalloproteinase 3 in vivo.

2. The method of claim 1 wherein the nucleobase polymer comprises GCCTCCTGAACTTCACTCCA (SEQ ID NO: 17).

3. The method of claim 1 wherein the nucleobase polymer comprises CCGGTGGUUTGUUGGU (SEQ ID NO: 12).

4. The method of claim 1 wherein the nucleobase polymer comprises monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl)morpholino) (piperazin-1-yl)phosphinate, or peptide nucleic acids and combinations thereof.

5. The method of claim 1 wherein the nucleobase polymer is 3' or 5' terminally conjugated to a hydrocarbon, polyethylene glycol, saccharide, polysaccharide, cell penetrating peptide, or combinations thereof.

6. The method of claim 5 wherein the cells penetrating peptide is a positively charged peptide, arginine-rich peptide, or oligoarginine peptide.

7. The method of claim 6 wherein the oligoarginine peptide is octa-arginine.

8. The method of claim 1, wherein the subject is a human.

9. The method of claim 1, wherein the pharmaceutical composition is administered in combination with a statin, atorvastatin, cerivastatin, fluvastatin, lovastatin, mevastatin, pitavastatin, pravastatin, rosuvastatin, simvastatin, ezetimibe, amlodipine, niacin, aspirin, omega-3 fatty acid, or combinations thereof.

10. A method of treating or preventing atherosclerosis comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUU-CUCUUGUCCUUCA UUCCACCGGAGUCUGUCU-CAUACCCAACCAGAUUUCAGUG-GAGUGAAGUUCAGGA GGCAUGGAGCUGACA wherein the nucleobase polymer binds sufficiently to prevent translation of tissue inhibitor of metalloproteinase 3 in vivo.

11. A method of treating or preventing peripheral vascular disease comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUU-CUCUU GUCCUUCAUUCCACCGGAGUCUGUCU-CAUACCCAACCAGAUUUCAGUGGAGUGAA GUUCAGGAGGCAUGGAGCUGACA wherein the nucleobase polymer binds sufficiently to prevent translation of tissue inhibitor of metalloproteinase 3 in vivo.

12. A method of treating or preventing coronary heart disease comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUU-CUCUUGUCCUUCA UUCCACCGGAGUCUGUCU-CAUACCCAACCAGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

13. A method of treating or preventing heart failure comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUU-CUCUUGUCCUUCAUUCCACCG GAGUCUGUCU-CAUACCCAACCAGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

14. A method of treating or preventing right ventricular hypertrophy comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAU-GUGCUUCUCUU GUCCUUCAUUCCACCGGAGUCU-GUCUCAUACCCAACCAGAUUUCAGUGGAGUGAA-GUUCAGGAGGCAUGGAGCUGACA wherein the nucleobase polymer binds sufficiently to prevent translation of tissue inhibitor of metalloproteinase 3 in vivo.

15. A method of treating or preventing cardiac dysrhythmia comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUU-CUCUUGUC CUUCAUUCCACCGGAGUCUGUCU-CAUACCCAACCAGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

16. A method of treating or preventing endocarditis comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUUCUC- UUGUCCUUCAUUCCACCGGAGUCUGUCU-CAUACCCAACC AGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

17. A method of treating or preventing inflammatory cardiomegaly comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUUCUCUU GUCCUUCAUUCCACCGGAGUCUGUCUCAUACCCAACCAGAUUUCAGUGGAGUGAAGUUCAGGAGGCAUGGAGCUGACA wherein the nucleobase polymer binds sufficiently to prevent translation of tissue inhibitor of metalloproteinase 3 in vivo.

18. A method of treating or preventing myocarditis comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUUCUCUUGUCCUUCAUUCCA CCGGAGUCUGUCUCAUACCCAACCAGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

19. A method of treating or preventing vascular heart disease comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUUCUCUU GUCCUUCAUUCCACCGGAGUCUGUCU-CAUACCCAACCAGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

20. A method of treating or preventing stroke comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUUCUCUU-GUCCUUCAUUCCACCGGAGUCUGUCUCAUACC-CAACCAGAUUUCAGUGGAGUGAAGUUCAGGAGG-CAUGGAGCUGACA wherein the nucleobase polymer binds sufficiently to prevent translation of tissue inhibitor of metalloproteinase 3 in vivo.

21. A method of treating or preventing cerebrovascular disease comprising administering an effective amount of a pharmaceutical composition comprising a single stranded nucleobase polymer to a subject in need thereof, wherein the single stranded nucleobase polymer binds miR-205 (SEQ ID NO: 11) AAAGAUCCUCAGACAAUCCAUGUGCUU-CUCUU GUCCUUCAUUCCACCGGAGUCUGUCU-CAUACCCAACCAGAUUUCAGUG-GAGUGAAGUUCAGGAGGCAUGGAGCUGACA wherein the nucleobase polymer binds sufficiently to prevent translation of tissue inhibitor of metalloproteinase 3 in vivo.

* * * * *